(12) United States Patent
Xie et al.

(10) Patent No.: US 12,275,726 B2
(45) Date of Patent: *Apr. 15, 2025

(54) AURORA KINASE INHIBITORS AND USE THEREOF

(71) Applicant: WIGEN BIOMEDICINE TECHNOLOGY (SHANGHAI) CO., LTD., Shanghai (CN)

(72) Inventors: Yuli Xie, Shanghai (CN); Houxing Fan, Shanghai (CN); Lihui Qian, Shanghai (CN)

(73) Assignee: WIGEN BIOMEDICINE TECHNOLOGY (SHANGHAI) CO., LTD., Shanghai (CN)

( * ) Notice: Subject to any disclaimer, the term of this patent is extended or adjusted under 35 U.S.C. 154(b) by 610 days.

This patent is subject to a terminal disclaimer.

(21) Appl. No.: 17/640,813

(22) PCT Filed: Dec. 2, 2020

(86) PCT No.: PCT/CN2020/133235
§ 371 (c)(1),
(2) Date: Mar. 5, 2022

(87) PCT Pub. No.: WO2021/110009
PCT Pub. Date: Jun. 10, 2021

(65) Prior Publication Data
US 2022/0324857 A1 Oct. 13, 2022

(30) Foreign Application Priority Data
Dec. 3, 2019 (CN) .......................... 201911256773.5

(51) Int. Cl.
*C07D 417/14* (2006.01)
*A61P 35/00* (2006.01)
*C07D 401/14* (2006.01)

(52) U.S. Cl.
CPC ............ *C07D 417/14* (2013.01); *A61P 35/00* (2018.01); *C07D 401/14* (2013.01)

(58) Field of Classification Search
CPC ...... C07D 401/14; C07D 417/14; A61P 35/00
See application file for complete search history.

(56) References Cited

U.S. PATENT DOCUMENTS

2016/0137628 A1* 5/2016 Henry ..................... A61P 35/00
546/194

FOREIGN PATENT DOCUMENTS

| CN | 101103017 A | 1/2008 |
|---|---|---|
| CN | 101405282 A | 4/2009 |
| CN | 104159893 A | 11/2014 |
| CN | 107108567 A | 8/2017 |
| EA | 018128 B1 | 5/2013 |
| EP | 2821406 A1 | 1/2015 |
| EP | 4001276 A1 | 5/2022 |
| JP | 2010540455 A | 12/2010 |
| JP | 2015518053 A | 6/2015 |
| JP | 2016539942 A | 12/2016 |
| JP | 2019517595 A | 6/2019 |
| WO | 0190121 A2 | 11/2001 |
| WO | 0192282 A2 | 12/2001 |
| WO | 2007027248 A2 | 3/2007 |
| WO | 2008026768 A1 | 3/2008 |
| WO | 2009104802 A1 | 8/2009 |
| WO | 2013129443 A1 | 9/2013 |
| WO | 2014168947 A2 | 10/2014 |
| WO | 2016077161 A1 | 5/2016 |
| WO | 2021147974 A1 | 7/2021 |

OTHER PUBLICATIONS

Meanwell, Chemical Research in Toxicology, v29, pp. 564-616 (2016). (Year: 2016).*
Vasilevich, et al.; Chemical Biology & Drug Design, v88, pp. 54-65 (2016). (Year: 2016).*
Natalya I. Vasilevich et al, "General Ser/Thr Kinases Pharmacophore Approach for Selective Kinase Inhibitors Search as Exemplified by Design of Potent and Selective Aurora A Inhibitors" Chem Biol Drug Des 2016; 88: 54-65 (Jan. 30, 2016).
Tanaka J C et al:"Photoreceptor Channel Activation by Nucleotide Derivatives" Biochemistry,, vol. 28, No. 7, Apr. 4, 1989 (Apr. 4, 1989), pp. 2776-2784, XP000611451, ISSN: 0006-2960, DOI: 10.1021/B100433A006.
Katharina Werner et al: "Quantification of CAMP and CGMP analogs in intact cells: pitfalls in enzyme immunoassays for cyclic nucleotides" Naunyn-Schmiedeberg's Archives of Pharmacology, Springer, Berlin, DE, vol. 384, No. 2, Jun. 29, 2011 (Jun. 29, 2011), pp. 169-176, XP019932461, ISSN: 1432-1912, DOI: 10.1007/S00210-011-0662-6.
Parker William B et al: "Effect of 9-Benzyl-9-deazaguanine, a Potent Inhibitor of Furine Nucleoside Phosphorylase, on the Cytotoxicity and Metabolism of 6-Thio-2 'deoxyguanosinel", Cancer Research, Jan. 1, 1994 (Jan. 1, 1994), pp. 1742-1745, XP055971940.

(Continued)

*Primary Examiner* — Jeffrey S Lundgren
*Assistant Examiner* — W. Justin Youngblood
(74) *Attorney, Agent, or Firm* — SZDC Law PC

(57) ABSTRACT

The invention relates to a type of novel pyridine compound and a preparation method and application thereof. Specifically, the invention relates to a compound of formula (1) and a preparation method thereof, and an application of the compound of formula (1) and pharmaceutically acceptable salts thereof as aurora kinase inhibitors in preparation of anti-tumor drugs.

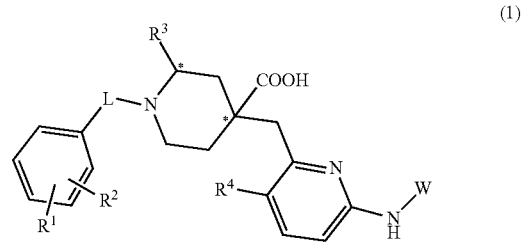

(1)

7 Claims, No Drawings

(56) References Cited

OTHER PUBLICATIONS

Nicholas C.K. Valerie et al: NUDT 15 Hydrolyzes 6-ThioDeoxyGTP to Mediate the Anticancer Efficacy of 6-Thioguanine Cancer Research, vol. 76, No. 18, Sep. 15, 2016 (Sep. 15, 2016), pp. 5501-5511, XP055647183, 2019 San Antonio Breast Cancer Symposium, San Antonio, Texas ISSN: 0008-5472, DOI: 10.1158/0008-5472.CAN-16-0584.

Breter et al: "The quantitative determination of metabolites of 6-mercaptopurine in biological materials. VI. Evidence for post-transcriptional modification of 6-thioguanosine residues in RNA from L5178Y cells treated with 6-mercaptopurine" Biochimica Et Biophysica Acta. Gene Structure and Expression, Elsevier, Amsterdam, NL, vol. 825, No. 1, May 24, 1985 (May 24, 1985), pp. 39-44, XP025221353, ISSN: 0167-4781, DOI: 10.1016/0167-4781 (85) 90077-6.

Tay B S et al: "Inhibition of phosphoribosyl pyrophosphate amidotransferase from Ehrlich ascites-tumour cells by thiopurine nucleotides" Biochemical Pharmacology, Elsevier, US, vol. 18, No. 4, Apr. 1, 1969 (Apr. 1, 1969), pp. 936-938, XP025904349, ISSN: 0006-2952, DOI: 10.1016/0006-2952(69)90069-0.

Natalya I. Vasilevich et al., "General Ser/Thr Kinase Pharmacophore Approach for Selective Kinase Inhibitors Search as Exemplified by Design of Potent and Selective Aurora A Inhibitors", Chemical Biology & Drug Design, vol. 88, No. 1, Jan. 30, 2016, pp. 54-65.

* cited by examiner

AURORA KINASE INHIBITORS AND USE THEREOF

The present application is the National Stage Application of PCT/CN2020/133235, filed on Dec. 2, 2020, which claims the benefits of Chinese Patent Application CN 201911256773.5 filed on Dec. 3, 2019, the content of which is incorporated herein by reference in its entirety.

FIELD OF THE INVENTION

The present invention relates to the field of medicinal chemistry, and particularly to a series of compounds with inhibition effect against aurora kinase, and the preparation method and use thereof.

BACKGROUND OF THE INVENTION

Aurora kinases are threonine/serine protein kinases that play a critical role in such important mitotic events as centrosome replication, bipolar spindle formation, chromosomal rearrangement and chromosome checkpoint monitoring (*Cancer Metastasis Rev.*, 2003, 22, 451). Currently, it has been known that there are 3 structurally and functionally highly related aurora kinase subtypes in human cells, namely Aurora-A, Aurora-B and Aurora-C. Aurora-A is located around the centrosome in the mitosis prophase, in the microtubules near the spindle in the metaphase, and on polar microtubules in the anaphase and telophase. It is mainly responsible for centrosome replication and separation, bipolar spindle aggregation, mitotic entry and exit, maturation of centrosomes and assembly of spindles (*Nat. Rev. Cancer*, 2005, 5, 42). Aurora-B is located in the centromere region of the chromosome during early stage of mitosis, and moves from the centromere to the microtubule in the anaphase. Aurora-B regulates centromere function, chromosome arrangement and separation, spindle checkpoint and cytokinesis (*Mol. Cancer Thu.*, 2009, 8, 2046-2056). Aurora-C is expressed at a high level in testis and may play a special role in male animals (*Proc Natl Acad Sci USA*, 2002, 99 (24): 15440-15445).

The gene encoding Aurora-A is localized at 20q13.2, a region which is generally amplified in many tumors, such as breast cancer, colon cancer, ovarian cancer and thyroid cancer. Overexpression of Aurora-A in cells causes cells to exhibit a variety of cancer cell characteristics such as centrosome amplification, aneuploidy, chromosome instability and lengthening of telomeres (*J. Cell Sci.*, 2007, 120, 2987). Overexpression of Aurora-A or co-expression with TPX-2 induces chromosome instability. In addition, Aurora-A also interferes with the function of important tumor inhibiting factors and pro-apoptotic proteins such as p53, wherein phosphorylation of p53 by Aurora-A at site Ser215 and at site Ser315 interferes with the normal function of p53 and causes its degradation, respectively.

Aurora-B is located at 17p13.1, and unlike Aurora-A, this region is not significantly amplified in many cancers other than brain glioma (*J. Clin. Pathol.*, 2007, 60(2): 218-221). However, mRNA and protein of Aurora-B are overexpressed in rapidly proliferating cells, such as many tumors, e.g., colon cancer, oral cancer and non-small cell lung cancer. Thus, tumor cells up-regulate the expression of Aurora family proteins in different ways. The chromosomal passenger protein complex (CPC) is an important complex for regulating mitosis, and Aurora-B is a core member thereof. The main substrates for Aurora-B phosphorylation include INCENP, CENP-A, Survivin, etc. Aurora-B regulates mitosis by phosphorylating its substrates. In addition to mitosis, Aurora-B overexpression also enhances the signal transduction pathway of the oncogene ras.

Unique pharmacological action mechanism and relation with malignant tumors cause aurora kinases to become important targets for research on anti-tumor drugs, and inhibitors of the Aurora kinase are also considered as novel anti-tumor drugs with good development prospect. LY-3295668 is an Aurora-A kinase inhibitor containing a main ring of pyridine (WO2016077161) and is now in phase 1 of clinic trial. LY-3295668 has the following structural formula:

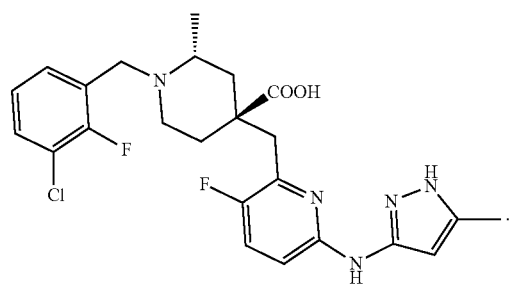 [SMILES: Cc1cc(Nc2ccc(F)c(C[C@]3(C(=O)O)CCN(Cc4cccc(Cl)c4F)[C@H](C)C3)n2)n[nH]1]

However, LY-3295668 and other Aurora-A kinase inhibitors have several disadvantages, such as insufficient Aurora kinase activity, poor oral absorption property and limited in vivo anti-tumor activity. Therefore, in view of the problems of existing aurora kinase inhibitors, finding a novel aurora inhibitor with higher in vitro and in vivo activity is of great significance.

SUMMARY OF THE INVENTION

The present invention provides a novel series of aurora kinase inhibitors with a structure shown as formula (1) or optical isomers, crystalline forms or pharmaceutically acceptable salts or esters thereof:

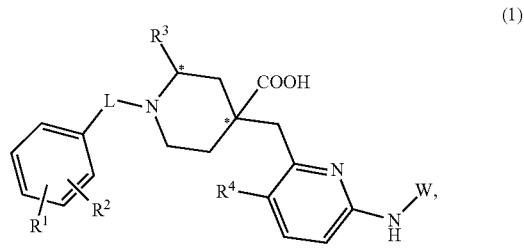

wherein in the formula (1):
"*" indicates a chiral center;
L is $CH_2$ or CO;
$R^1$ and $R^2$ are independently H, halogen, CN, C1-C3 alkyl, C3-C6 cycloalkyl, C1-C3 alkoxy, C1-C3 haloalkyl or C1-C3 haloalkoxy;
$R^3$ is C2-C3 alkyl, C3-C6 cycloalkyl, C1-C3 haloalkyl, —(C1-C3)alkyl-OH, —(C1-C3)alkyl-(C1-C3)alkoxy, —(C1-C3)alkyl-CN or —(C1-C3)alkyl-$NR^5R^6$, wherein $R^5$ and $R^6$ are independently H or C1-C3 alkyl, or $R^5$ and $R^6$ form a 4-7 membered heterocycloalkyl together with an N atom;
$R^4$ is H or F;

W is

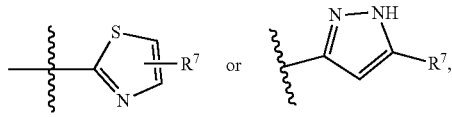

wherein R⁷ is H, C1-C3 alkyl or C3-C6 cycloalkyl.

In another preferred embodiment, in the formula (1),

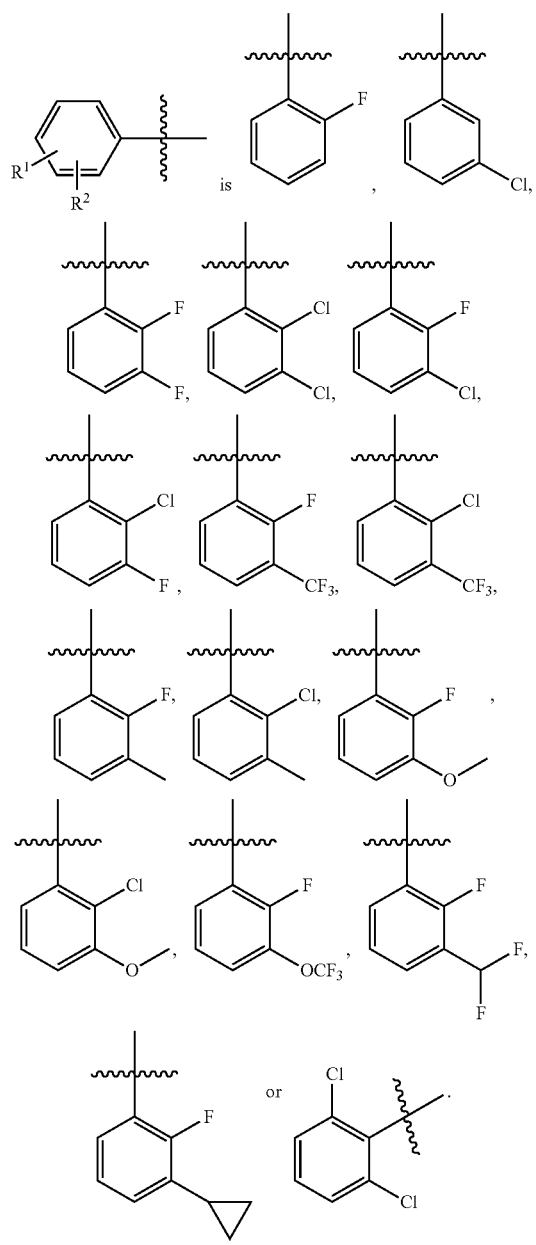

In another preferred embodiment, in the formula (1), R³ is the following groups: Et, $^n$-Pr, $^i$-Pr,

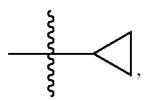

$CH_2F$, $CHF_2$, $CF_3$, $CH_2OH$, $CH_2OMe$, $CH_2OEt$, $CH_2CN$,

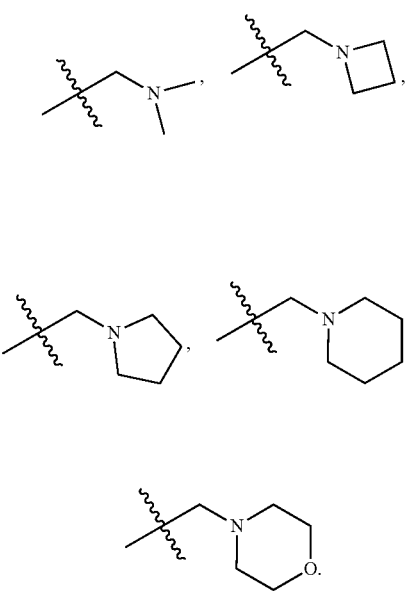

In another preferred embodiment, in the formula (1), W is the following groups:

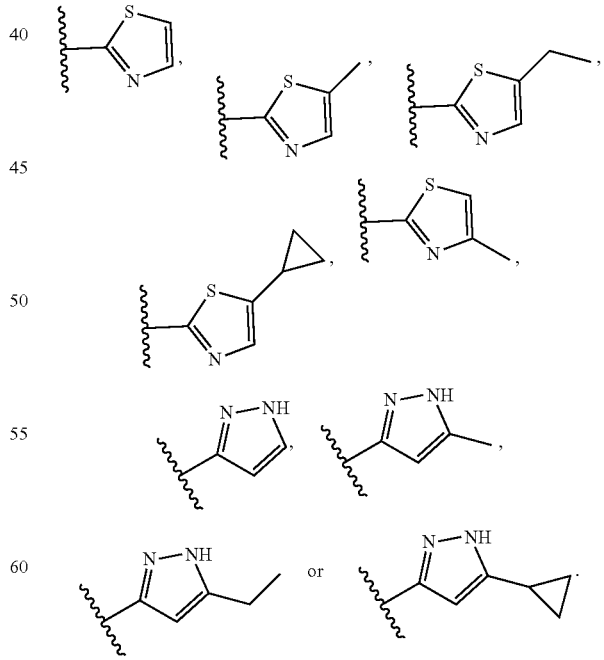

In various embodiments, representative compounds of the present invention have one of the following structures:

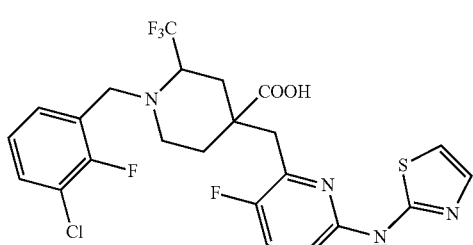
1
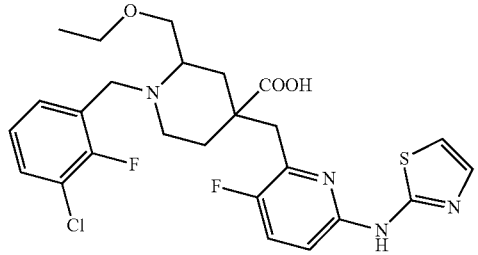
7
2
8
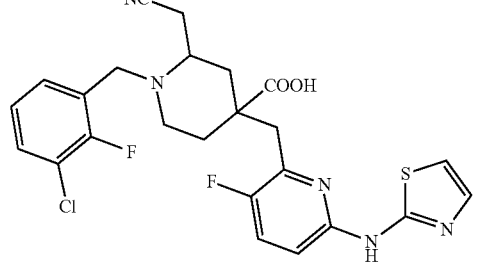
3
9
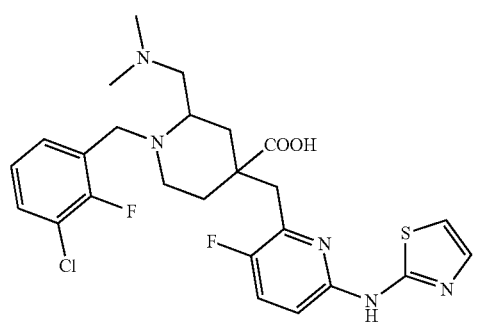
4
10
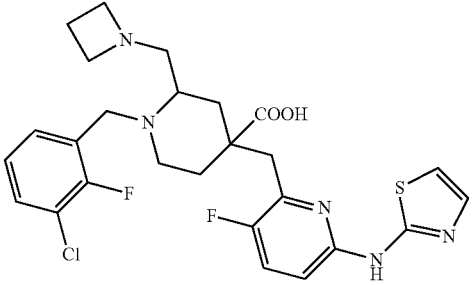
5
11
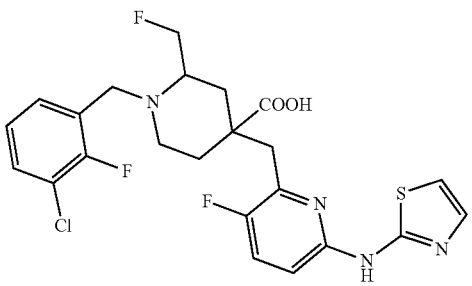
6

12
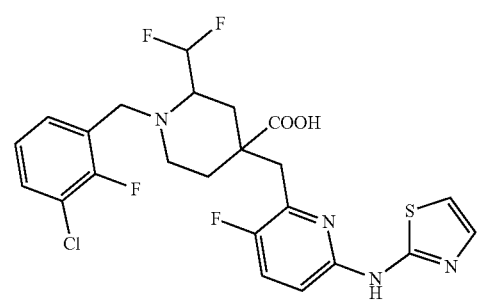
13
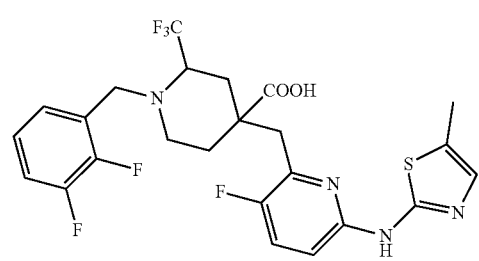
14
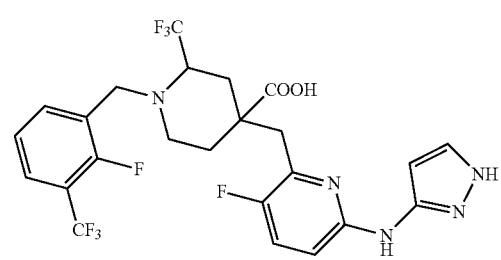
15
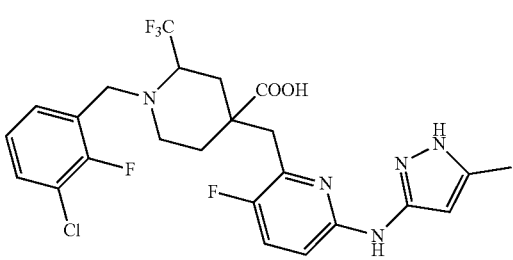
16
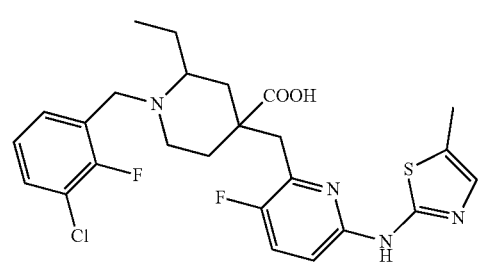
17
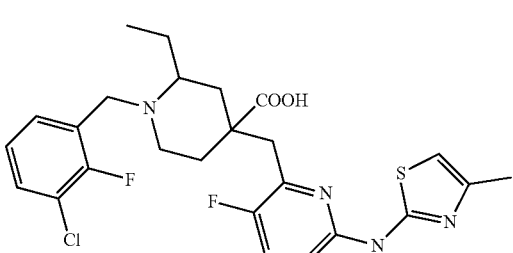
18
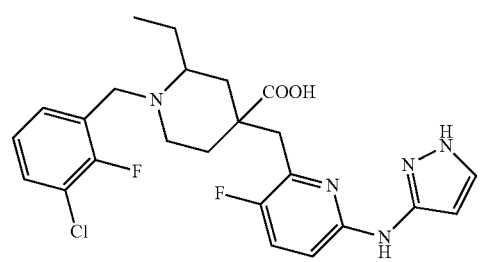
19
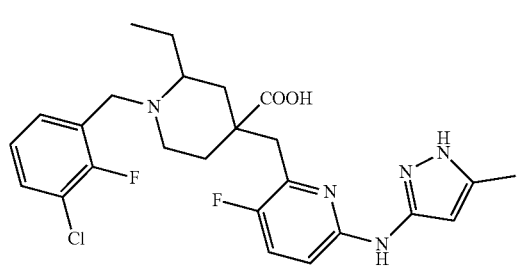
20
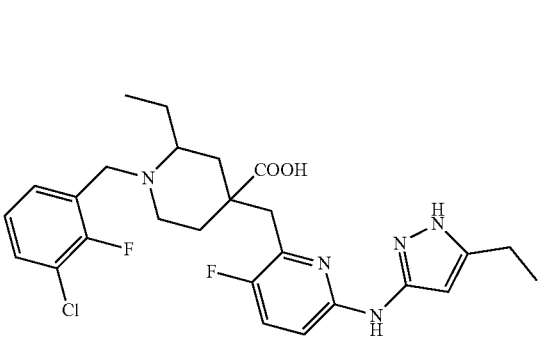
21
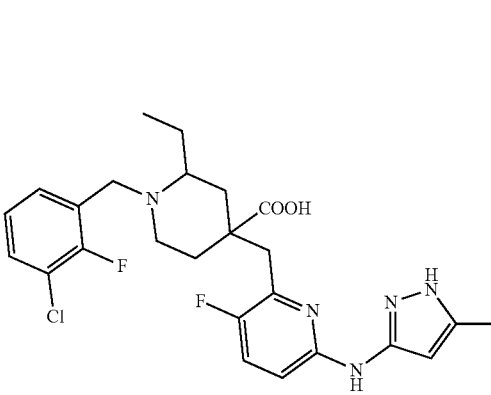
22
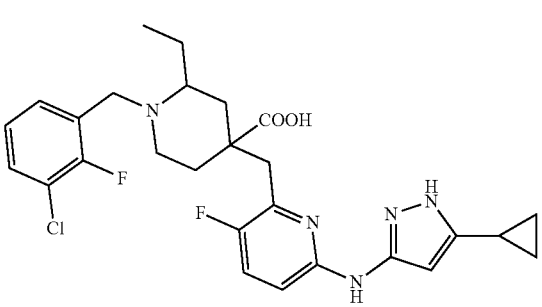

23
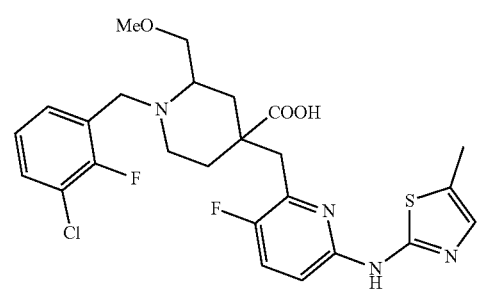
24
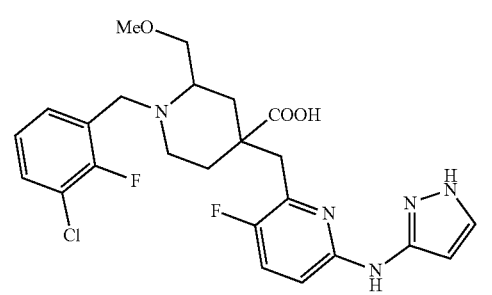
25
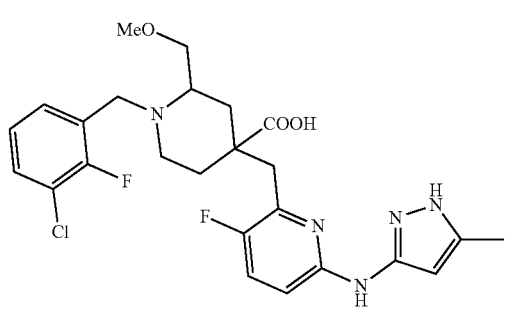
26
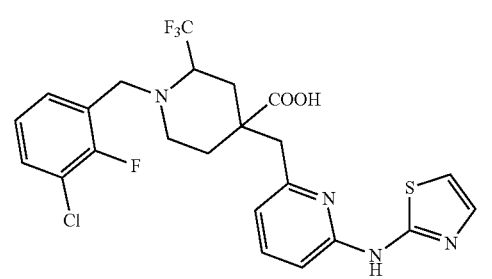
27
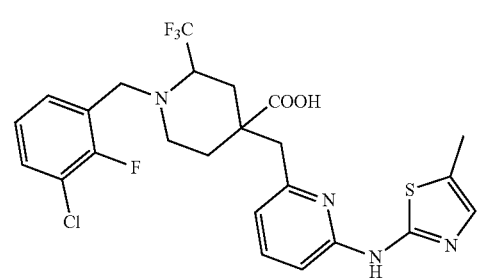
28
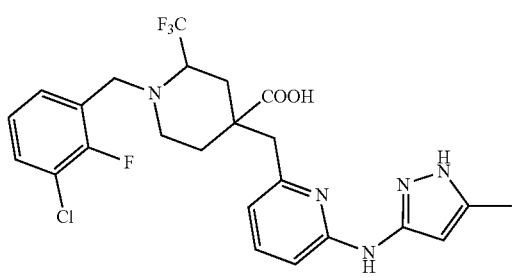
29
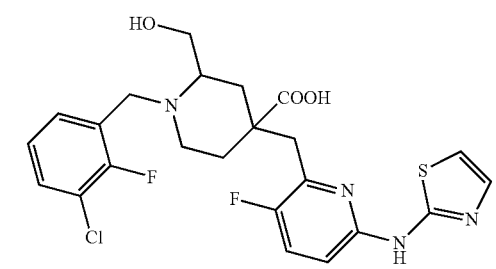
30
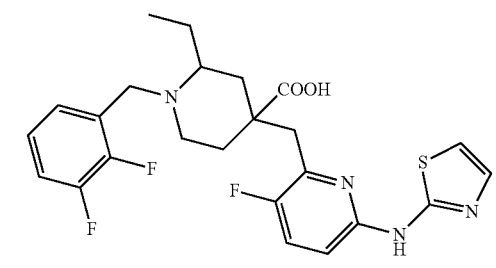
31
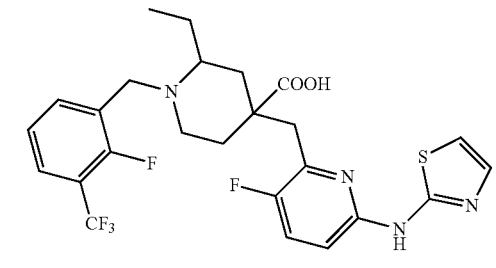
32
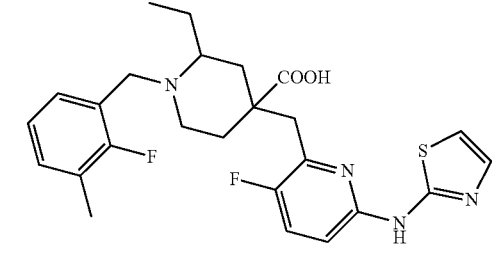
33
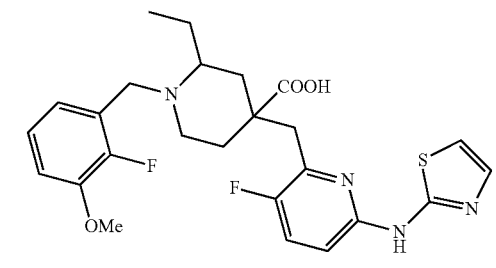

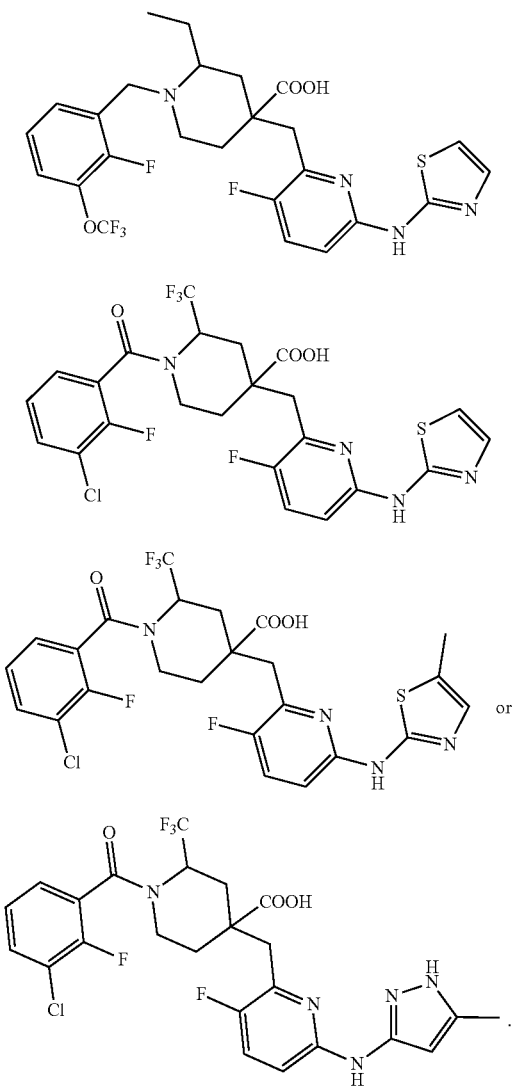

Another purpose of the present invention is to provide a pharmaceutical composition comprising a pharmaceutically acceptable excipient or carrier and a compound of formula (1) or optical isomers, crystalline forms or pharmaceutically acceptable salts or esters thereof disclosed herein as an active ingredient.

Still another purpose of the present invention is to provide use of the compound or the optical isomers, the crystalline forms or the pharmaceutically acceptable salts or esters thereof described above in preparing drugs for treating Aurora-related diseases, especially anti-tumor drugs.

Synthesis of the Compounds

The preparation methods of the compounds of the general formula (1) are described hereafter in detail, but these specific methods do not constitute any limitations of the present invention.

The compound of formula (1) described above may be synthesized using standard synthetic techniques or well-known techniques in combination with the methods described herein. In addition, solvents, temperatures and other reaction conditions mentioned herein may vary. Starting materials for the synthesis of the compounds in Table 1 may be obtained synthetically or from commercial sources, such as, but not limited to, Aldrich Chemical Co. (Milwaukee, Wis.) or Sigma Chemical Co. (St. Louis, Mo.). The compounds described herein and other related compounds having different substituents may be synthesized using well-known techniques and starting materials, including those found in March, ADVANCED ORGANIC CHEMISTRY, 4$^{th}$ Ed., (Wiley 1992); Carey and Sundberg, ADVANCED ORGANIC CHEMISTRY, 4$^{th}$ Ed., Vols. A and B (Plenum 2000, 2001), and Green and Wuts, PROTECTIVE GROUPS IN ORGANIC SYNTHESIS, 3$^{rd}$ Ed., (Wiley 1999). General methods for the preparation of the compounds can be varied by using suitable reagents and conditions for introducing different groups into the formulas provided herein.

In one aspect, the compound of formula (1) described herein is prepared according to the well-known methods. However, the conditions of the process, such as reactants, solvents, bases, amounts of the compound used, temperature of the reactions and time required for the reactions and the like are not limited to the following explanations. The compounds disclosed herein may also be conveniently prepared by optionally in combination with various synthetic methods described herein or well-known methods, and such combinations can be easily determined by those skilled in the art to which the present invention pertains. In the other aspect, the present invention also provides a method of the compounds of formula (1), which are prepared by the following method A, method B or method C:

The method A includes the following steps: firstly, a compound A is reduced by hydrogenation into a compound B in the presence of a catalyst, the compound B and a fragment S1 generate a compound C under an alkaline condition, the compound C is butted with a fragment S2 under an alkaline condition to generate a compound D, the compound D reacts with a fragment S3 under an alkaline condition and in the presence of a metallic palladium catalyst and a ligand to generate a compound E, and the compound E is subjected to ester hydrolysis reaction under an acidic or alkaline condition to obtain the target compound (1a).

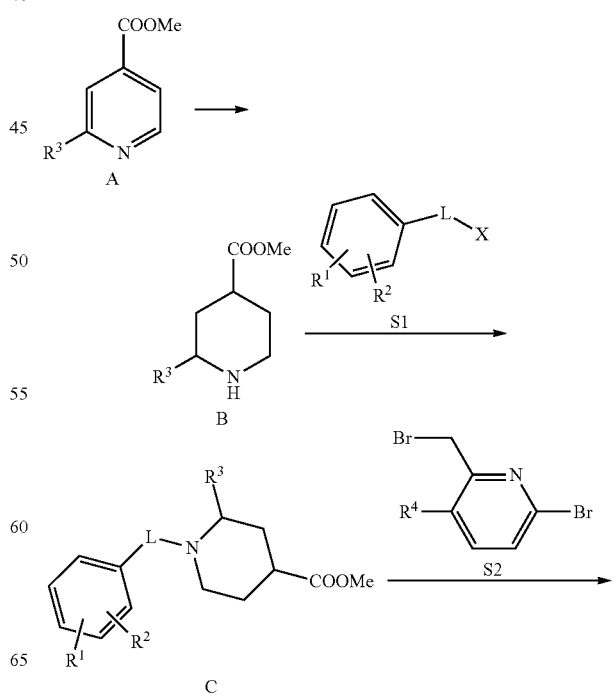

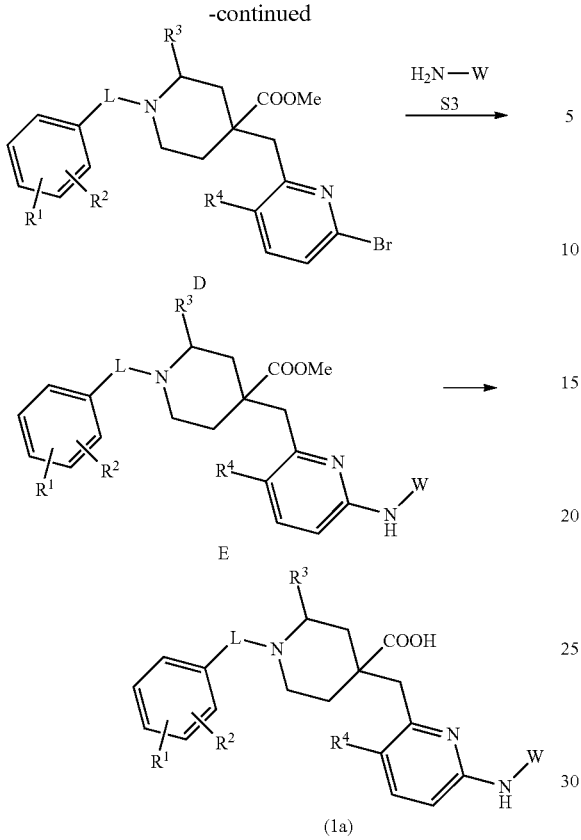

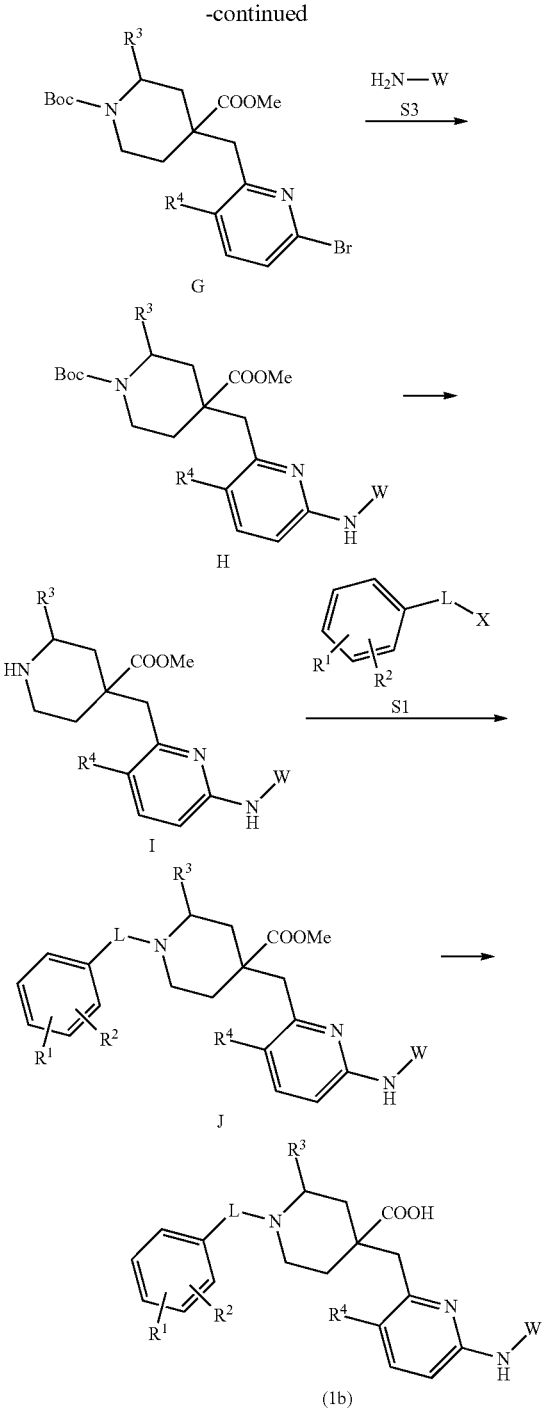

In the above reaction, $R^1$, $R^2$, $R^3$, $R^4$, L and W are as defined above, and X is I, Br, Cl, OTf, OH or the like.

The method B includes the following steps: firstly, the compound B is Boc protected under proper conditions to obtain a compound F, the compound F reacts with the fragment S2 under an alkaline condition to obtain a compound G, the compound G reacts with the fragment S3 in the presence of a metallic palladium catalyst and a ligand to generate a compound H, the compound H is subjected to Boc deprotection under an acidic condition to obtain a compound I, the compound I reacts with the fragment S1 under an alkaline condition to generate a compound J, and the compound J is subjected to ester hydrolysis reaction under an acidic or alkaline condition to obtain the target compound (1b).

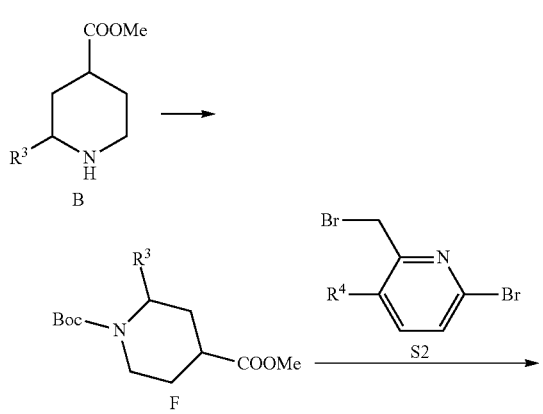

In the above reaction, $R^1$, $R^2$, $R^3$, $R^4$, L and W are as defined above, and X is I, Br, Cl, OTf, OH or the like.

The method C includes the following steps: firstly, the compound G is subjected to Boc deprotection under an acidic condition to obtain a compound K, the compound K is condensed with the fragment S1 to obtain a compound L, the compound L reacts with the fragment S3 in the presence of a metallic palladium catalyst and a ligand to generate a compound M, and the compound M is subjected to ester hydrolysis reaction under an acidic or alkaline condition to obtain the target compound (1c).

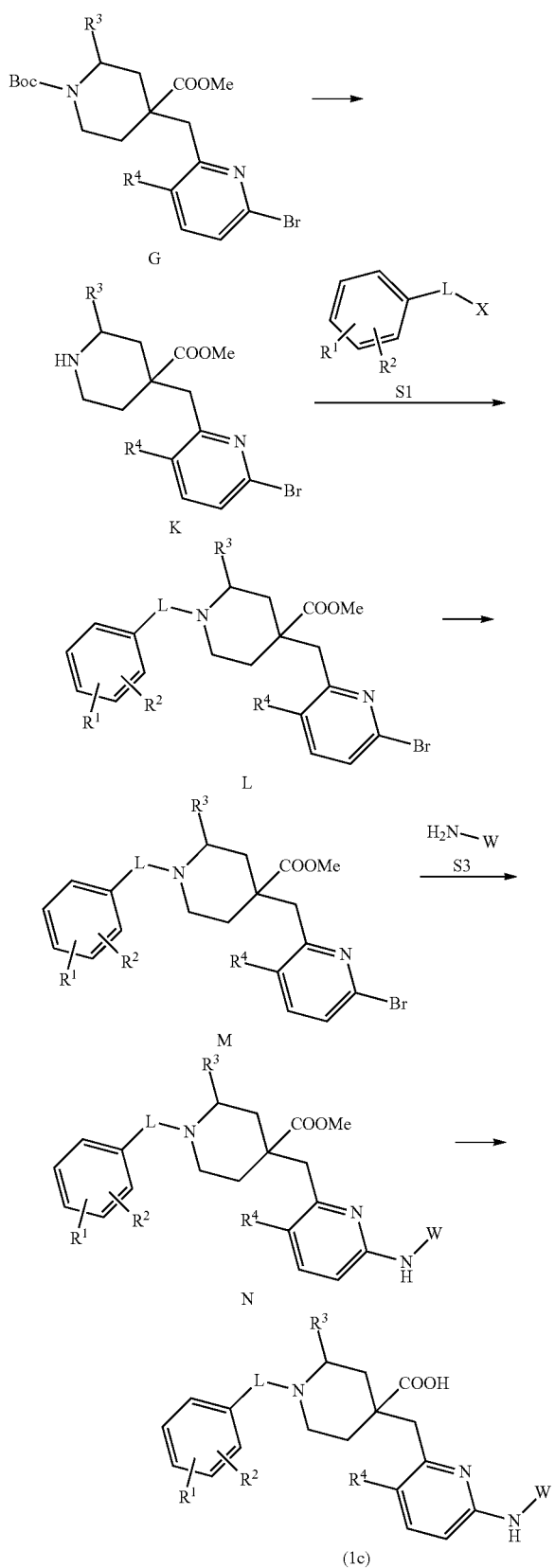

In the above reaction, $R^1$, $R^2$, $R^3$, $R^4$, L and W are as defined above, and X is I, Br, Cl, OTf, OH or the like.

Further Forms of Compounds

In this patent specification, including the appended claims, the aforementioned substituents have the following meanings:

"Halogen" (or halo) refers to fluorine, chlorine, bromine or iodine. The term "halo" before a group name indicates that the group is partially or fully halogenated, that is, substituted in any combination by F, Cl, Br, or I, preferably by F or Cl. "C1-3 alkyl" refers to straight or branched alkyl groups containing 1 to 3 carbon atoms. "C2-3 alkyl" refers to straight or branched alkyl groups containing 2 to 3 carbon atoms. "C1-3 haloalkyl" means that the C1-3 alkyl as defined above contains one or more halogen atom substituents. "C3-6 cycloalkyl" refers to a non-aromatic cyclic group containing 3 to 6 carbon atoms. "C1-3 alkoxy" refers to a C1-3 alkyl-O-group bonded to the parent moiety through an oxygen. —(C1-C3)alkyl-OH, (C1-C3)alkyl-(C1-C3)alkoxy, —(C1-C3)alkyl-CN and —(C1-C3)alkyl-NR$^5$R$^6$ refer to groups formed by linking the C1-C3 alkyl defined above with OH, (C1-C3)alkoxy, CN and NR$^5$R$^6$ groups, respectively, and bonded to the parent moiety through a (C1-C3)alkyl group. "4-7 membered heterocycloalkyl" refers to a non-aromatic saturated cyclic group containing from 4 to 7 ring atoms.

The term "pharmaceutically acceptable salt" refers to a form of a compound that does not cause significant irritation to the organism for drug administration or eliminate the biological activity and properties of the compound. The salt of the compound of the present invention refers to a salt conventionally used in the field of organic chemistry, and can be, for example, a base addition salt of a carboxyl group in the case of having a carboxyl group, and an acid addition salt of an amino group or a basic heterocyclic group in the case of having an amino group or a basic heterocyclic group.

Examples of the base addition salt can be alkali metal salts such as sodium salts and potassium salts; alkaline earth metal salts such as calcium salts and magnesium salts; ammonium salts; organic amine salts such as trimethylamine salts, triethylamine salts, dicyclohexylamine salts, ethanolamine salts, diethanolamine salts, triethanolamine salts, procaine salts, N,N-dibenzylethylenediamine salts, meglumine salts, arginine salts and lysine salts and the like.

Examples of the acid addition salt can be inorganic acid salts such as hydrochloride, sulfate, nitrate and phosphate; organic acid salts such as acetate, formate, maleate, fumarate, citrate, oxalate and ascorbate; sulfonate such as methanesulfonate, benzenesulfonate and p-toluenesulfonate, and the like.

It should be understood that references to pharmaceutically acceptable salts include solvent addition forms or crystal forms, especially solvates or polymorphs. A solvate contains either stoichiometric or non-stoichiometric amount of solvent and is selectively formed during crystallization with pharmaceutically acceptable solvents such as water and ethanol. Hydrates are formed when the solvent is water, or alcoholates are formed when the solvent is ethanol. Solvates of the compound of formula (1) are conveniently prepared or formed according to methods described herein. For example, the hydrate of the compound of formula (1) is conveniently prepared by recrystallization in a mixed solvent of water/organic solvent, wherein the organic solvent used includes, but is not limited to, dioxane, tetrahydrofuran, ethanol or methanol. Furthermore, the compounds mentioned herein can exist in both non-solvated and solvated forms. In general, the solvated forms are considered equivalent to the non-solvated forms for purposes of the compounds and methods provided herein.

In other specific embodiments, the compounds of formula (1) are prepared in different forms, including but not limited to amorphous, pulverized and nanoparticle forms. In addition, the compound of formula (1) includes crystalline forms, and may also be polymorphs. Polymorphs include different lattice arrangements of the same elements of a compound. Polymorphs usually have different X-ray diffraction patterns, infrared spectra, melting points, density, hardness, crystalline forms, optical and electrical properties, stability and solubility. Different factors such as recrystallization solvent, crystallization rate and storage temperature may lead to monocrystalline form being dominant.

In another aspect, the compound of formula (1) has one or more stereocenters and thus occurs in the form of a racemate, racemic mixture, single enantiomer, diastereomeric compound and single diastereomer. Asymmetric centers that may be present depend on the nature of the various substituents on the molecule. Each of these asymmetric centers will independently produce two optical isomers, and all possible optical isomers, diastereomeric mixtures and pure or partially pure compounds are included within the scope of the present invention. The present invention is meant to include all such isomeric forms of these compounds.

Therapeutic Use

The compounds or compositions described herein can generally be used to inhibit aurora kinase, and thus can be used to treat one or more disorders related to aurora kinase activity. Therefore, in certain embodiments, the present invention provides a method for treating an aurora kinase-mediated disorder, which includes the step of administering to a patient in need thereof a compound disclosed herein or a pharmaceutically acceptable composition thereof.

Cancers that can be treated with the compound disclosed herein include, but are not limited to, hematological malignancies (leukemias, lymphomas, myelomas including multiple myeloma, myelodysplastic syndrome and myeloproliferative syndrome), solid tumors (carcinomas such as prostate, breast, lung, colon, pancreas, kidney, ovary and soft tissue carcinomas, osteosarcoma and interstitial tumors), and the like.

Route of Administration

The compound and the pharmaceutically acceptable salt thereof disclosed herein can be prepared into various preparations which include the compound or the pharmaceutically acceptable salt thereof disclosed herein in a safe and effective amount range and a pharmaceutically acceptable excipient or carrier, wherein the "safe and effective amount" means that the amount of the compound is sufficient to significantly improve the condition without causing serious side effects. The safe and effective amount of the compound is determined according to the age, condition, course of treatment and other specific conditions of a treated subject.

The "pharmaceutically acceptable excipient or carrier" refers to one or more compatible solid or liquid fillers or gel substances which are suitable for human use and must be of sufficient purity and sufficiently low toxicity. "Compatible" means that the components of the composition are capable of intermixing with the compound disclosed herein and with each other, without significantly diminishing the pharmaceutical efficacy of the compound. Examples of pharmaceutically acceptable excipients or carrier moieties are cellulose and its derivatives (e.g., sodium carboxymethylcellulose, sodium ethylcellulose or cellulose acetate), gelatin, talc, solid lubricants (e.g., stearic acid or magnesium stearate), calcium sulfate, vegetable oil (e.g., soybean oil, sesame oil, peanut oil or olive oil), polyols (e.g., propylene glycol, glycerol, mannitol or sorbitol), emulsifiers (e.g., Tween®), wetting agents (e.g., sodium lauryl sulfate), colorants, flavoring agents, stabilizers, antioxidants, preservatives, pyrogen-free water, and the like.

When the compound disclosed herein is administered, it may be administered orally, rectally, parenterally (intravenously, intramuscularly or subcutaneously) or topically.

Solid dosage forms for oral administration include capsules, tablets, pills, pulvises and granules. In these solid dosage forms, the active compound is mixed with at least one conventional inert excipient (or carrier), such as sodium citrate or dicalcium phosphate, or with the following ingredients: (a) fillers or extenders, such as starch, lactose, sucrose, glucose, mannitol and silicic acid; (b) binders, such as hydroxymethyl cellulose, alginate, gelatin, polyvinylpyrrolidone, sucrose and acacia; (c) humectants, such as glycerol; (d) disintegrants, such as agar, calcium carbonate, potato or tapioca starch, alginic acid, certain complex silicates and sodium carbonate; (e) solution retarders, such as paraffin; (f) absorption accelerators, such as quaternary ammonium compounds; (g) wetting agents, such as cetyl alcohol and glycerol monostearate; (h) adsorbents, such as kaolin; and (i) lubricants, such as talc, calcium stearate, magnesium stearate, solid polyethylene glycol and sodium lauryl sulfate, or mixtures thereof. In the case of capsules, tablets and pills, the dosage forms may also include buffers.

Solid dosage forms such as tablets, dragees, capsules, pills and granules can be prepared using coatings and shells such as enteric coatings and other materials well known in the art. They may include opacifying agents, and the active compound or compound in such a composition may be released in a certain part of the digestive tract in a delayed manner. Examples of embedding components that can be used are polymeric substances and wax-based substances. If necessary, the active compound can also be in microcapsule form with one or more of the above-mentioned excipients.

Liquid dosage forms for oral administration include pharmaceutically acceptable emulsions, solutions, suspensions, syrups and elixirs. In addition to the active compound, the liquid dosage form may include inert diluents commonly used in the art, such as water or other solvents, solubilizers and emulsifiers, for example, ethanol, isopropanol, ethyl carbonate, ethyl acetate, propylene glycol, 1,3-butanediol, dimethylformamide, and oils, especially cottonseed oil, groundnut oil, corn germ oil, olive oil, castor oil and sesame oil, or mixtures of these substances.

Besides such inert diluents, the composition may also include adjuvants, such as wetting agents, emulsifiers, suspending agents, sweeteners, flavoring agents, and perfuming agents.

Suspensions, in addition to the active compound, may include suspending agents, such as ethoxylated isostearyl alcohols, polyoxyethylene sorbitol and sorbitan esters, microcrystalline cellulose, aluminum methylate and agar, or mixtures of these substances.

Compositions for parenteral injection may include physiologically acceptable sterile aqueous or anhydrous solutions, dispersions, suspensions or emulsions, and sterile powders for redissolving into sterile injectable solutions or dispersions. Suitable aqueous and non-aqueous carriers, diluents, solvents or excipients include water, ethanol, polyols and suitable mixtures thereof.

Dosage forms for topical administration of the compound disclosed herein include ointments, pulvises, patches, sprays and inhalants. The active ingredient is mixed under sterile conditions with a physiologically acceptable carrier and any preservatives, buffers or propellants that may be required if necessary.

The compound disclosed herein may be administered alone or in combination with other pharmaceutically acceptable compounds.

When the pharmaceutical composition is used, a safe and effective amount of the compound disclosed herein is administered to a mammal (such as a human) to be treated, wherein the administration dosage is a pharmaceutically effective administration dosage. For a human with a body weight of 60 kg, the daily administration dosage is usually 1-1000 mg, preferably 10-500 mg. In determining a specific dosage, such factors as the route of administration, the health condition of the patient and the like will also be considered, which are well known to skilled physicians.

The above features mentioned in the present invention or those mentioned in the examples may be combined arbitrarily. All the features disclosed in this specification may be used with any composition form and the various features disclosed in this specification may be replaced with any alternative features that provide the same, equivalent or similar purpose. Thus, unless otherwise expressly stated, the features disclosed are merely general examples of equivalent or similar features.

Various specific aspects, features and advantages of the compounds, methods and pharmaceutical compositions described above are set forth in detail in the following description, which makes the present invention clear. It should be understood that the detailed description and examples below describe specific embodiments for reference only. After reading the description of the present invention, those skilled in the art can make various changes or modifications to the present invention, and such equivalents also fall within the scope of the present invention defined herein.

In all examples, melting points were measured using an X-4 melting point apparatus with the thermometer uncalibrated; $^1$H-NMR spectra were recorded with a Varian Mercury 400 nuclear magnetic resonance spectrometer, and chemical shifts are expressed in δ (ppm); silica gel for separation was 200-300 mesh silica gel if not specified, and the ratio of the eluents was volume ratio.

Following abbreviations are used in the present invention: ACN represents acetonitrile; Ar represents argon; (Boc)$_2$O represents di-tert-butyl dicarbonate; CDCl$_3$ represents deuterated chloroform; CD$_3$OD represents deuterated methanol; DCM represents dichloromethane; DIPEA represents diisopropylethylamine; Diox or Dioxane represents 1,4-dioxane; DMAP represents 4-dimethylaminopyridine; DMF represents dimethylformamide; DMSO represents dimethyl sulfoxide; EA represents ethyl acetate; h represents hour; K$_2$CO$_3$ represents potassium carbonate; KI represents potassium iodide; K$_3$PO$_4$ represents potassium phosphate; LC-MS stands for liquid-mass spectrometry; LDA represents lithium diisopropylamide; LiOH represents lithium hydroxide; mL represents milliliter; MeOH represents methanol; min represents minute; MS represents mass spectrum; NMR stands for nuclear magnetic resonance; Pd$_2$(dba)$_3$ represents tris(dibenzylideneacetone)dipalladium; PE represents petroleum ether; PtO$_2$ represents platinum dioxide; THF represents tetrahydrofuran; Xantphos represents 4,5-bis(diphenylphosphino)-9,9-dimethylxanthene.

DETAILED DESCRIPTION OF THE INVENTION

Example 1. Synthesis of 1-(3-chloro-2-fluorobenzyl)-4-((3-fluoro-6-(thiazol-2-ylamino) pyridin-2-yl) methyl)-2-(trifluoromethyl)piperidine-4-carboxylic acid (compound 1)

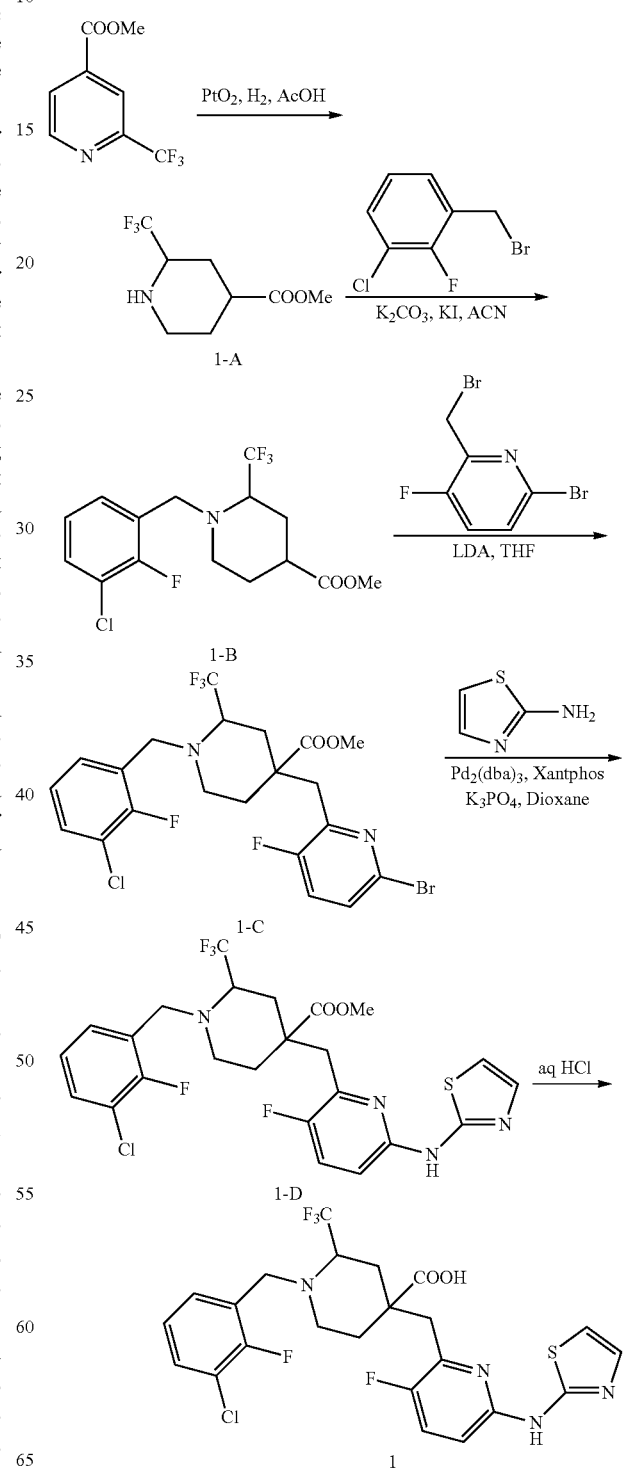

Methyl 2-(trifluoromethyl)piperidine-4-carboxylate (1-A)

Methyl 2-trifluoromethylpyridine-4-carboxylate (5 g, 24.374 mmol), HOAc (100 mL) and PtO$_2$ (0.5 g) were added to a 500 mL single-necked flask, and the reaction system was purged with H$_2$ three times, warmed to 60° C. and vigorously stirred for 1-3 days while the flask was connected to a hydrogen bag. After the completion of the reaction as detected by LC-MS, the reaction system was cooled to room temperature and subjected to diatomite assisted filtration, and the filtrate was concentrated. The residue was added to EA (100 mL), and saturated sodium bicarbonate solution (50 mL) was slowly added at room temperature. The mixture was stirred, liquid separation was performed, and the aqueous phase was extracted with EA (25 mL×2). The organic phases were combined, washed with saturated sodium chloride solution, dried over anhydrous sodium sulfate and filtered, and the filtrate was concentrated to give the product in the form of a light brown oil (4.8 g, 93% yield), ESI-MS m/z: 212.0 [M+H]$^+$.

Methyl 1-(3-chloro-2-fluorobenzyl)-2-(trifluoromethyl)piperidine-4-carboxylate (1-B)

1-A (4.8 g, 22.729 mmol), 2-fluoro-3-chlorobenzyl bromide (5.59 g, 25.0 mmol), K$_2$CO$_3$ (9.41 g, 68.2 mmol), KI (200 mg) and ACN (100 mL) were added to a 250 mL single-necked flask, and the reaction system was warmed to reflux and stirred for 20 h under Ar atmosphere. After the completion of the reaction as detected by LC/MS, EA (50 mL)/ice (100 mL) was added to the reaction system. The resulting reaction system was stirred, liquid separation was performed, and the aqueous phase was extracted with EA (50 mL). The organic phases were combined, washed with saturated sodium chloride solution and concentrated, and the residue was purified by column chromatography (EA/PE=0/20 to 1/20) to give the product in the form of a colorless oil (4.3 g, 53.5% yield), ESI-MS m/z: 354.0 [M+H]$^+$.

Methyl 4-((6-bromo-3-fluoropyridin-2-yl)methyl)-1-(3-chloro-2-fluorobenzyl)-2-(trifluoromethyl)piperidine-4-carboxylate (1-C)

1-B (4.3 g, 12.156 mmol) and anhydrous THF (86 mL) were added to a 250 mL three-necked flask, and the reaction system was cooled to −60° C. under Ar atmosphere. LDA (9.1 mL, 2 M in THF, 18.2 mmol) was added dropwise slowly, and the temperature was kept below −45° C. during the dropwise addition. After the dropwise addition was completed, the mixed solution was stirred at −50±10° C. for 2 h. A solution of 6-bromo-2-(bromomethyl)-3-fluoropyridine (3.923 g, 14.587 mmol) in THF (20 mL) was then added dropwise at −60±10° C. After the dropwise addition was completed, the resulting reaction system was stirred at −60±10° C. for 1 h, and then slowly warmed to room temperature and reacted for 1 h. After the completion of the reaction as detected by TLC (EA/PE=1/10) and LC-MS, ammonium chloride solution (50 mL) was added to quench the reaction, and EA (50 mL×2) was added for extraction. The organic phases were combined, washed with saturated sodium chloride solution (50 mL×2) and concentrated, and the residue was purified by column chromatography (EA/PE=1/20 to 1/10) to give the product in the form of a light brown liquid (5.12 g, 77.9% yield), ESI-MS m/z: 541.1/543.1 [M+H]$^+$.

Methyl 1-(3-chloro-2-fluorobenzyl)-4-((3-fluoro-6-(thiazol-2-ylamino)pyridin-2-yl)meth-yl)-2-(trifluoromethyl)piperidine-4-carboxylate (1-D)

1-C (2 g, 3.697 mmol), 2-aminothiazole (444 mg, 4.44 mmol), anhydrous K$_3$PO$_4$ (1.96 g, 9.243 mmol), Xantphos (214 mg, 0.37 mmol) and Dioxane (50 mL) were added to a 250 mL single-necked flask. After purge with Ar, Pd$_2$(dba)$_3$ (174 mg, 0.19 mmol) was added, and the reaction system was warmed to reflux under Ar atmosphere and reacted for 12 h. After the completion of the reaction as detected by LC-MS, the reaction system was cooled to room temperature and filtered, and the filtrate was concentrated to dryness. The residue was purified by column chromatography (DCM/MeOH=100/1 to 40/1) to give the product in the form of a brown oil (1.62 g, 78.1% yield), ESI-MS m/z: 561.1 [M+H]$^+$.

1-(3-chloro-2-fluorobenzyl)-4-((3-fluoro-6-(thiazol-2-ylamino)pyridin-2-yl)methyl)-2-(trifluoromethyl)piperidine-4-carboxylic acid (1)

1-D (1.62 g, 2.888 mmol), water (32 mL) and concentrated HCl (32 mL) were added to a 100 mL single-necked flask, and the reaction system was refluxed at 105° C. for 20 h. After the completion of the reaction as detected by LC/MS, the reaction solution was concentrated to dryness under reduced pressure, and the residue was added to ACN (30 mL). The mixture was slurried at room temperature and subjected to suction filtration, and the filter cake was washed with ACN (5 mL×2) and dried to give the product in the form of an off-white solid (622 mg, 39.4% yield).

$^1$H NMR (400 MHz, CD3OD) δ7.75 (td, J=8.8, 1.5 Hz, 1H), 7.60 (dd, J=4.4, 1.9 Hz, 1H), 7.57-7.46 (m, 2H), 7.28 (dd, J=4.4, 1.7 Hz, 1H), 7.26-7.20 (m, 1H), 7.17 (dd, J=8.9, 3.1 Hz, 1H), 4.92-4.85 (m,1H), 4.47 (d, J=13.8 Hz, 1H), 4.26 (dd, J=40.5, 13.7 Hz, 2H), 3.51-3.33 (m, 2H), 3.23-3.17 (m, 1H), 2.39 (dd, J=15.1, 9.1 Hz, 1H), 2.25 (dd, J=15.2, 4.4 Hz, 1H), 2.17-2.04 (m, 1H), 1.95 (d, J=14.7 Hz, 1H); ESI-MS m/z: 547.1 [M+H]$^+$.

By chiral separation, four different optical isomers of compound 1 can be obtained, and the structural formulas are as follows:

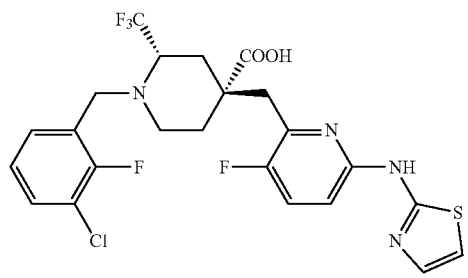

1-1

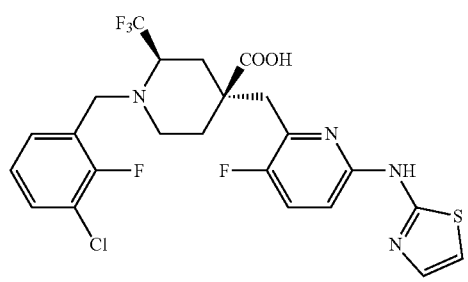

1-2

-continued 1-3

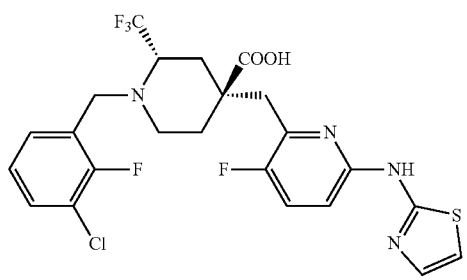

-continued 1-4

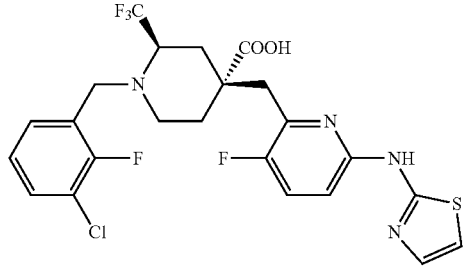

Examples 2-28. Synthesis of Compounds 2-28

The target compounds 2-28 were obtained according to a similar synthesis method as in Example 1 using different starting materials.

TABLE 1

| Compound | Compound structure | Name | [M + H]⁺ |
|---|---|---|---|
| 2 | 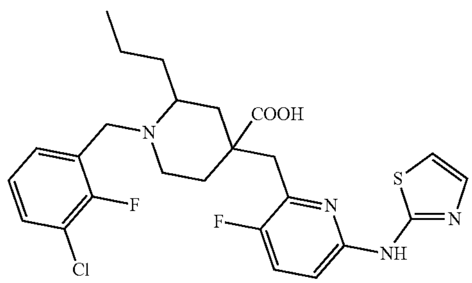 [SMILES: CCCC1CC(Cc2nc(Nc3nccs3)ccc2F)(C(=O)O)CCN1Cc1cccc(Cl)c1F] | 1-(3-chloro-2-fluorobenzyl)-4-((3-fluoro-6-(thiazol-2-ylamino)pyridin-2-yl)methyl)-2-propylpiperidine-4-carboxylic acid | 521.2 |
| 3 | 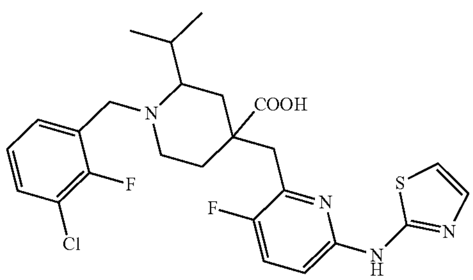 [SMILES: CC(C)C1CC(Cc2nc(Nc3nccs3)ccc2F)(C(=O)O)CCN1Cc1cccc(Cl)c1F] | 1-(3-chloro-2-fluorobenzyl)-4-((3-fluoro-6-(thiazol-2-ylamino)pyridin-2-yl)methyl)-2-isopropylpiperidine-4-carboxylic acid | 521.2 |
| 4 | 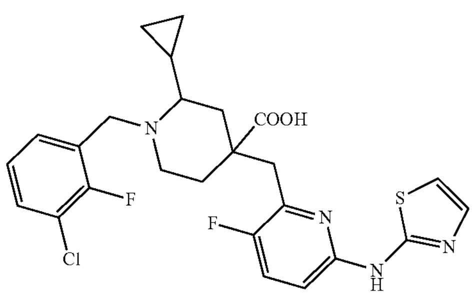 [SMILES: O=C(O)C1(Cc2nc(Nc3nccs3)ccc2F)CCN(Cc2cccc(Cl)c2F)C(C2CC2)C1] | 1-(3-chloro-2-fluorobenzyl)-2-cyclopropyl-4-((3-fluoro-6-(thiazol-2-ylamino)pyridin-2-yl)methyl)piperidine-4-carboxylic acid | 519.1 |
| 5 | 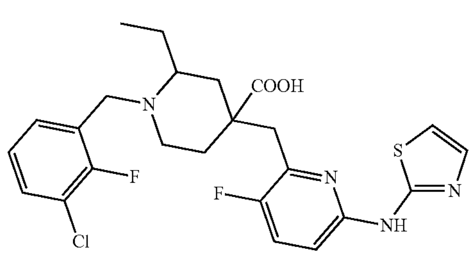 [SMILES: CCC1CC(Cc2nc(Nc3nccs3)ccc2F)(C(=O)O)CCN1Cc1cccc(Cl)c1F] | 1-(3-chloro-2-fluorobenzyl)-2-ethyl-4-((3-fluoro-6-(thiazol-2-ylamino)pyridin-2-yl)methyl)piperidine-4-carboxylic acid | 507.1 |

TABLE 1-continued

| Compound | Compound structure | Name | [M + H]+ |
|---|---|---|---|
| 6 | 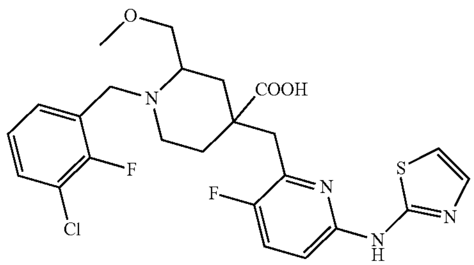 [SMILES: COCC1CC(Cc2nc(Nc3nccs3)ccc2F)(C(=O)O)CCN1Cc1cccc(Cl)c1F] | 1-(3-chloro-2-fluorobenzyl)-4-((3-fluoro-6-(thiazol-2-ylamino)pyridin-2-yl)methyl)-2-(methoxymethyl)piperidine-4-carboxylic acid | 523.1 |
| 7 | 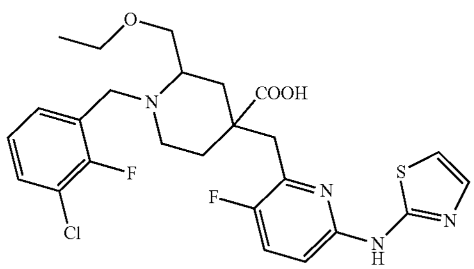 [SMILES: CCOCC1CC(Cc2nc(Nc3nccs3)ccc2F)(C(=O)O)CCN1Cc1cccc(Cl)c1F] | 1-(3-chloro-2-fluorobenzyl)-2-(ethoxymethyl)-4-((3-fluoro-6-(thiazol-2-ylamino)pyridin-2-yl)methyl)piperidine-4-carboxylic acid | 537.2 |
| 8 | 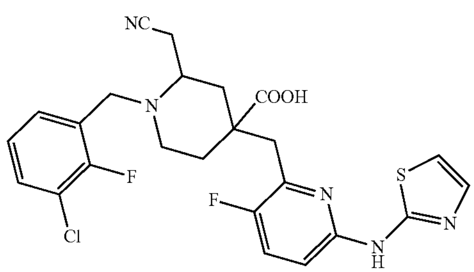 | 1-(3-chloro-2-fluorobenzyl)-2-(cyanomethyl)-4-((3-fluoro-6-(thiazol-2-ylamino)pyridin-2-yl)methyl)piperidine-4-carboxylic acid | 518.1 |
| 9 | 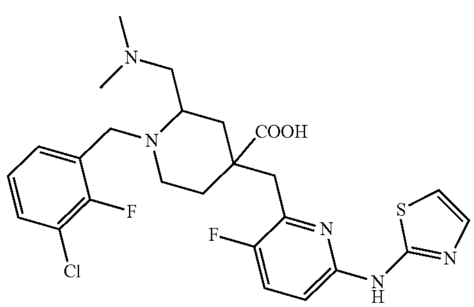 [SMILES: CN(C)CC1CC(Cc2nc(Nc3nccs3)ccc2F)(C(=O)O)CCN1Cc1cccc(Cl)c1F] | 1-(3-chloro-2-fluorobenzyl)-2-((dimethylamino)methyl)-4-((3-fluoro-6-(thiazol-2-ylamino)pyridin-2-yl)methyl)piperidine-4-carboxylic acid | 536.2 |
| 10 | 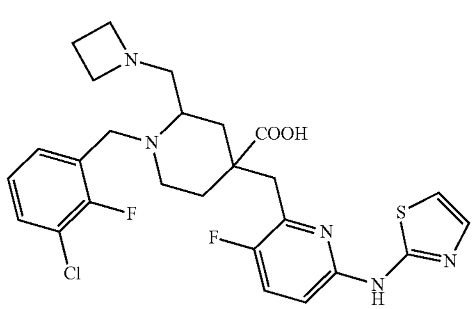 [SMILES: O=C(O)C1(Cc2nc(Nc3nccs3)ccc2F)CCN(Cc2cccc(Cl)c2F)C(CN2CCC2)C1] | 2-(azetidin-1-ylmethyl)-1-(3-chloro-2-fluorobenzyl)-4-((3-fluoro-6-(thiazol-2-ylamino)pyridin-2-yl)methyl)piperidine-4-carboxylic acid | 548.2 |

TABLE 1-continued

| Compound | Compound structure | Name | [M + H]+ |
|---|---|---|---|
| 11 | 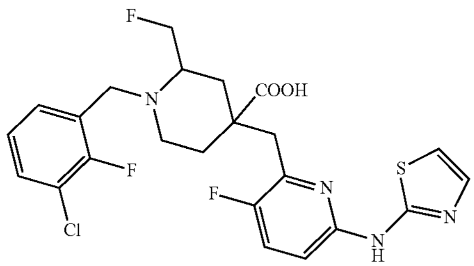 [SMILES: O=C(O)C1(Cc2nc(Nc3nccs3)ccc2F)CCN(Cc2cccc(Cl)c2F)C(CF)C1] | 1-(3-chloro-2-fluorobenzyl)-4-((3-fluoro-6-(thiazol-2-ylamino)pyridin-2-yl)methyl)-2-(fluoromethyl)piperidine-4-carboxylic acid | 511.1 |
| 12 | 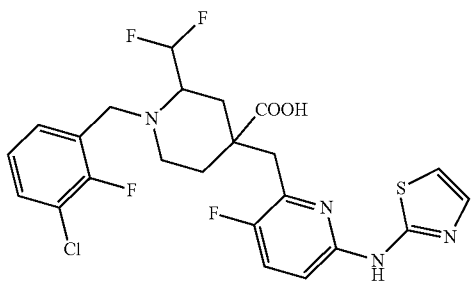 [SMILES: O=C(O)C1(Cc2nc(Nc3nccs3)ccc2F)CCN(Cc2cccc(Cl)c2F)C(C(F)F)C1] | 1-(3-chloro-2-fluorobenzyl)-2-(difluoromethyl)-4-((3-fluoro-6-(thiazol-2-ylamino)pyridin-2-yl)methyl)piperidine-4-carboxylic acid | 529.1 |
| 13 | 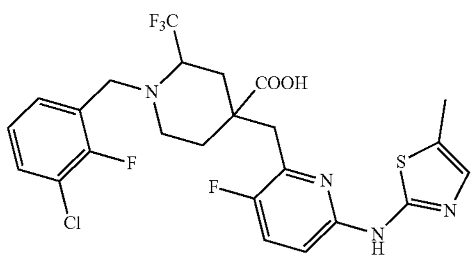 [SMILES: Cc1cnc(Nc2ccc(F)c(CC3(C(=O)O)CCN(Cc4cccc(Cl)c4F)C(C(F)(F)F)C3)n2)s1] | 1-(3-chloro-2-fluorobenzyl)-4-((3-fluoro-6-(5-methylthiazol-2-ylamino)pyridin-2-yl)methyl)-2-(trifluoromethyl)piperidine-4-carboxylic acid | 561.1 |
| 14 | 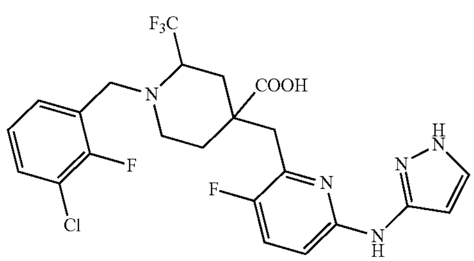 [SMILES: O=C(O)C1(Cc2nc(Nc3cc[nH]n3)ccc2F)CCN(Cc2cccc(Cl)c2F)C(C(F)(F)F)C1] | 4-((6-((1H-pyrazol-3-yl)amino)-3-fluoropyridin-2-yl)methyl)-1-(3-chloro-2-fluorobenzyl)-2-(trifluoromethyl)piperidine-4-carboxylic acid | 530.1 |
| 15 | 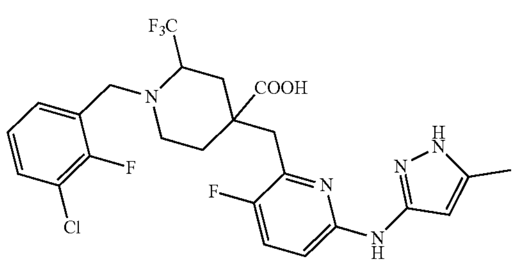 [SMILES: Cc1cc(Nc2ccc(F)c(CC3(C(=O)O)CCN(Cc4cccc(Cl)c4F)C(C(F)(F)F)C3)n2)n[nH]1] | 1-(3-chloro-2-fluorobenzyl)-4-((3-fluoro-6-((5-methyl-1H-pyrazol-3-yl)amino)pyridin-2-yl)methyl)-2-(trifluoromethyl)piperidine-4-carboxylic acid | 544.2 |
| 16 | 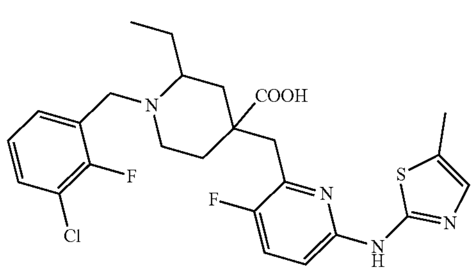 [SMILES: CCC1CC(Cc2nc(Nc3ncc(C)s3)ccc2F)(C(=O)O)CCN1Cc1cccc(Cl)c1F] | 1-(3-chloro-2-fluorobenzyl)-2-ethyl-4-((3-fluoro-6-((5-methylthiazol-2-yl)amino)pyridin-2-yl)methyl)piperidine-4-carboxylic acid | 521.2 |

TABLE 1-continued

| Compound | Compound structure | Name | [M + H]⁺ |
|---|---|---|---|
| 17 | 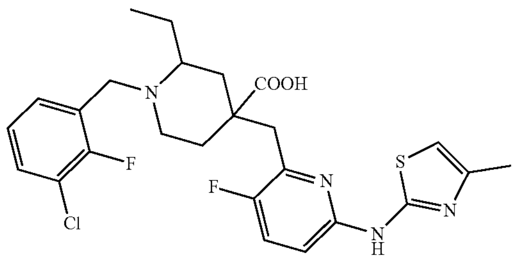 [SMILES: CCC1CC(Cc2nc(Nc3nc(C)cs3)ccc2F)(C(=O)O)CCN1Cc1cccc(Cl)c1F] | 1-(3-chloro-2-fluorobenzyl)-2-ethyl-4-((3-fluoro-6-((4-methylthiazol-2-yl)amino)pyridin-2-yl)methyl)piperidine-4-carboxylic acid | 521.2 |
| 18 | 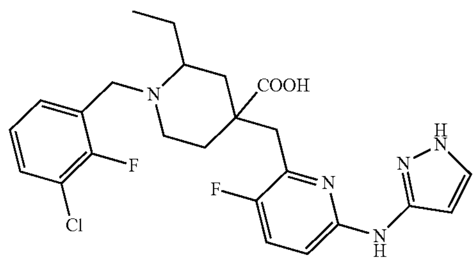 [SMILES: CCC1CC(Cc2nc(Nc3cc[nH]n3)ccc2F)(C(=O)O)CCN1Cc1cccc(Cl)c1F] | 4-((6-((1H-pyrazol-3-yl)amino)-3-fluoropyridin-2-yl)methyl)-1-(3-chloro-2-fluorobenzyl)-2-ethylpiperidine-4-carboxylic acid | 490.2 |
| 19 | 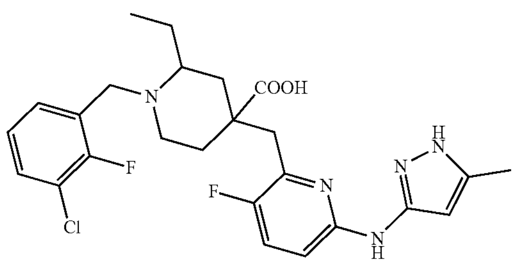 [SMILES: CCC1CC(Cc2nc(Nc3cc(C)[nH]n3)ccc2F)(C(=O)O)CCN1Cc1cccc(Cl)c1F] | 1-(3-chloro-2-fluorobenzyl)-2-ethyl-4-((3-fluoro-6-((5-methyl-1H-pyrazol-3-yl)amino)pyridin-2-yl)methyl)piperidine-4-carboxylic acid | 504.2 |
| 20 | 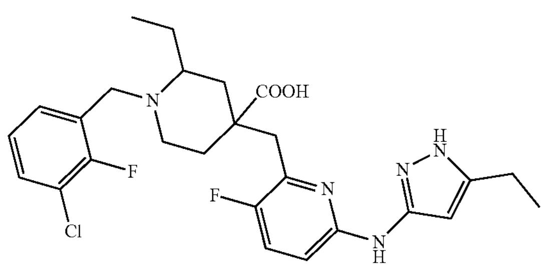 [SMILES: CCc1cc(Nc2ccc(F)c(CC3(C(=O)O)CCN(Cc4cccc(Cl)c4F)C(CC)C3)n2)n[nH]1] | 1-(3-chloro-2-fluorobenzyl)-2-ethyl-4-((6-((5-ethyl-1H-pyrazol-3-yl)amino)-3-fluoropyridin-2-yl)methyl)piperidine-4-carboxylic acid | 518.2 |
| 21 | 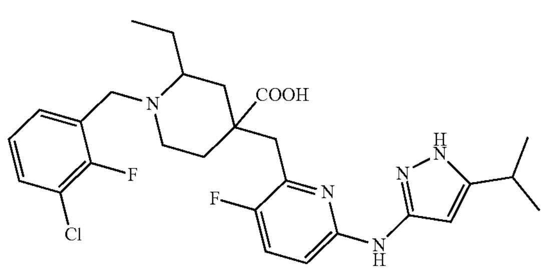 [SMILES: CCC1CC(Cc2nc(Nc3cc(C(C)C)[nH]n3)ccc2F)(C(=O)O)CCN1Cc1cccc(Cl)c1F] | 1-(3-chloro-2-fluorobenzyl)-2-ethyl-4-((6-((5-ethyl-1H-pyrazol-3-yl)amino)-3-fluoropyridin-2-yl)methyl)piperidine-4-carboxylic acid | 532.2 |
| 22 | 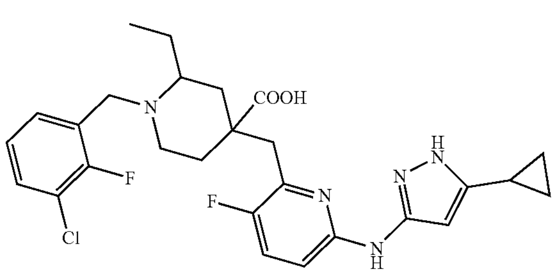 [SMILES: CCC1CC(Cc2nc(Nc3cc(C4CC4)[nH]n3)ccc2F)(C(=O)O)CCN1Cc1cccc(Cl)c1F] | 1-(3-chloro-2-fluorobenzyl)-4-((6-((5-isopropyl-1H-pyrazol-3-yl)amino)-3-fluoropyridin-2-yl)methyl)-2-ethylpiperidine-4-carboxylic acid | 530.2 |

TABLE 1-continued

| Compound | Name | [M + H]+ |
|---|---|---|
| 23 | 1-(3-chloro-2-fluorobenzyl)-4-((3-fluoro-6-(5-methylthiazol-2-ylamino)pyridin-2-yl)methyl)-2-(methoxymethyl)piperidine-4-carboxylic acid | 537.1 |
| 24 | 4-((6-((1H-pyrazol-3-yl)amino)-3-fluoropyridin-2-yl)methyl)-1-(3-chloro-2-fluorobenzyl)-2-(methoxymethyl)piperidine-4-carboxylic acid | 506.2 |
| 25 | 1-(3-chloro-2-fluorobenzyl)-4-((3-fluoro-6-((5-methyl-1H-pyrazol-3-yl)amino)pyridin-2-yl)methyl)-2-(methoxymethyl)piperidine-4-carboxylic acid | 520.2 |
| 26 | 1-(3-chloro-2-fluorobenzyl)-4-((6-(thiazol-2-ylamino)pyridin-2-yl)methyl)-2-(trifluoromethyl)piperidine-4-carboxylic acid | 529.1 |
| 27 | 1-(3-chloro-2-fluorobenzyl)-4-((6-(5-methylthiazol-2-ylamino)pyridin-2-yl)methyl)-2-(trifluoromethyl)piperidine-4-carboxylic acid | 543.1 |
| 28 | 1-(3-chloro-2-fluorobenzyl)-4-((6-((5-methyl-1H-pyrazol-3-yl)amino)pyridin-2-yl)methyl)-2-(trifluoromethyl)piperidine-4-carboxylic acid | 526.2 |

Example 29. Synthesis of 1-(3-chloro-2-fluorobenzyl)-2-ethyl-4-((3-fluoro-6-(thiazol-2-ylamino) pyridin-2-yl)methyl)piperidine-4-carboxylic acid (compound 29)

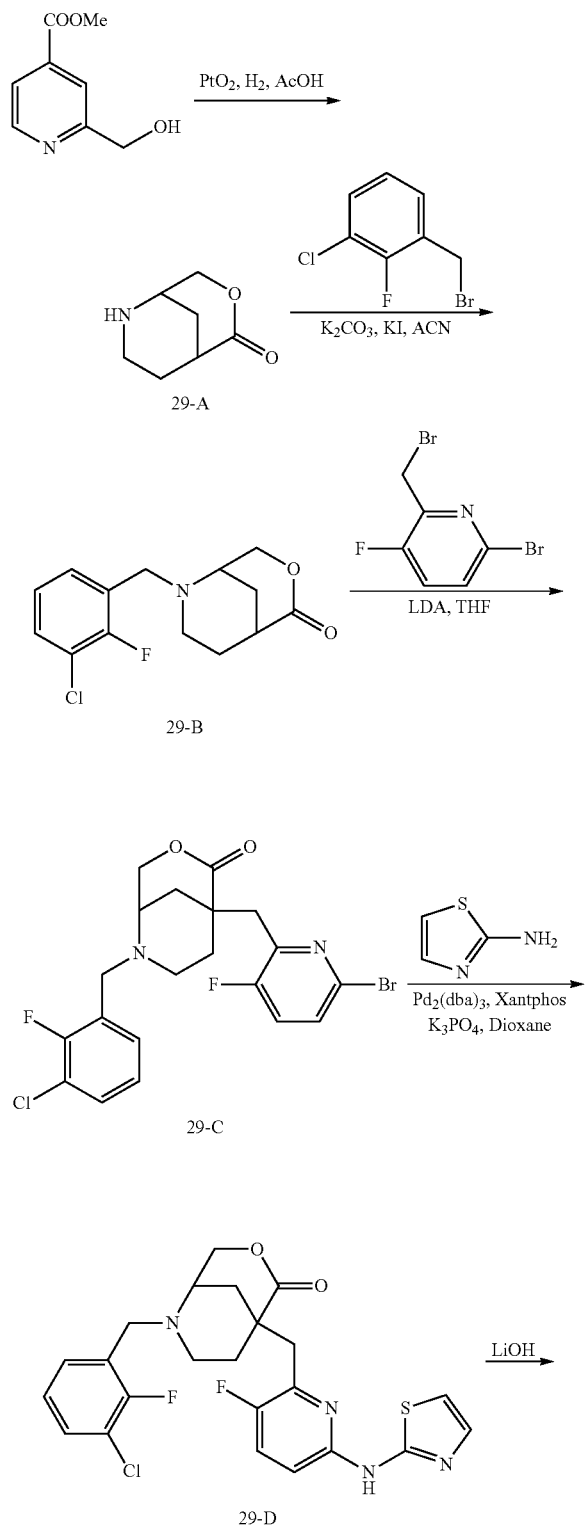

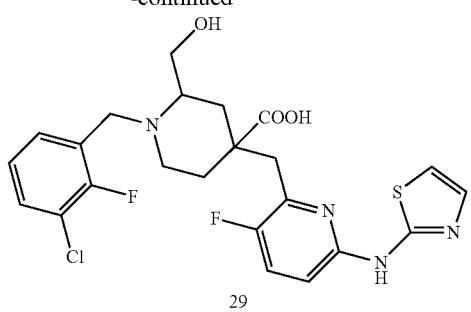

Using methyl 2-hydroxymethylpyridine-4-carboxylate as a starting material, an intermediate 2-(3-chloro-2-fluorobenzyl)-5-((3-fluoro-6-(thiazol-2-ylamino)pyridin-2-yl) methyl)-7-oxa-2-azabicyclo[3.3.1]nonyl-6-one (29-D) was obtained by the synthesis method in Example 1.

1-(3-chloro-2-fluorobenzyl)-2-ethyl-4-((3-fluoro-6-(thiazol-2-ylamino)pyridin-2-yl)methyl)piperidine-4-carboxylic acid (29)

29-D (25 mg, 0.051 mmol), THF (2 mL) and H$_2$O (1 mL) were added to a 10 mL single-necked flask, LiOH·H$_2$O (10.7 mg, 0.25 mmol) was then added at room temperature, and the reaction system was stirred at room temperature for 2 h. After the completion of the reaction as detected by LC-MS, the mixed solution was purified by Flash column chromatography to give the product (18 mg, 69.3% yield).

$^1$H NMR (400 MHz, CDCl$_3$) δ7.82 (t, J=8.9 Hz, 1H), 7.75 (t, J=7.8 Hz, 1H), 7.61 (d, J=4.4 Hz, 1H), 7.52 (t, J=6.9 Hz, 1H), 7.41 (d, J=7.9 Hz, 1H), 7.32 (d, J=4.3 Hz, 1H), 7.22 (dd, J=8.9, 3.0 Hz, 1H), 4.85-4.75 (m, 2H), 4.47 (d, J=13.6 Hz, 1H), 4.23 (d, J=11.4 Hz, 1H), 4.01 (d, J=12.0 Hz, 1H), 3.83-3.62 (m, 2H), 3.51-3.41 (m, 2H), 2.47-2.36 (m, 1H), 2.31-2.25 (m, 1H), 2.11-1.85 (m, 2H); ESI-MS m/z: 509.0 [M+H]$^+$.

Example 30. Synthesis of 1-(2,3-difluorobenzyl)-2-ethyl-4-((3-fluoro-6-(thiazol-2-ylamino) pyridin-2-yl)methyl)piperidine-4-carboxylic acid (compound 30)

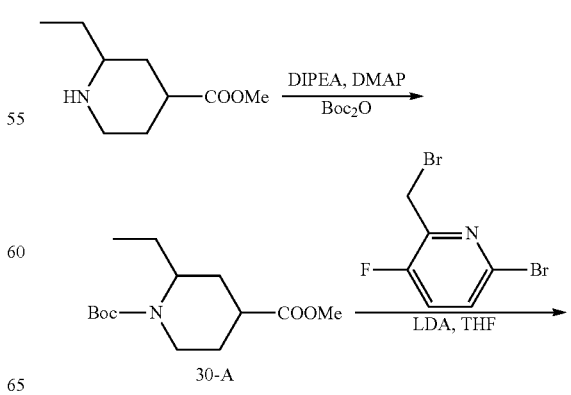

-continued

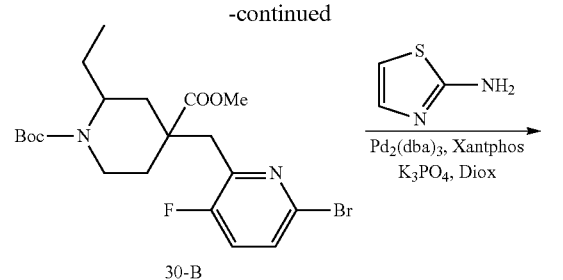

30-B

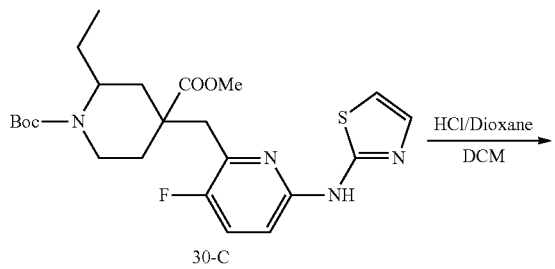

30-C

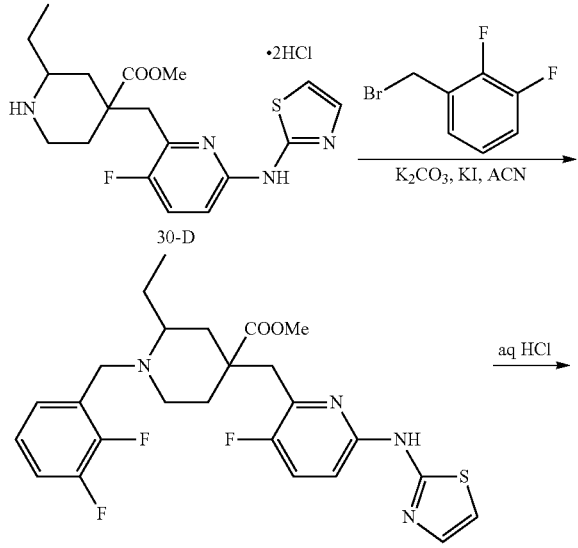

30-E

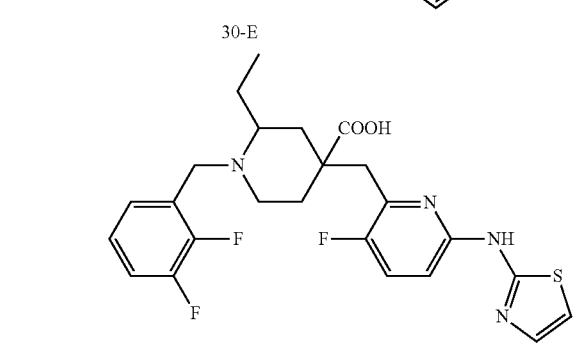

30

1-(tert-butyl)4-methyl-2-ethylpiperidine-1,4-dicarboxylate (30-A)

Methyl 2-ethylpiperidine-4-carboxylate (8.94 g, 52.24 mmol), DIPEA (20.3 g, 156.72 mmol), DMAP (638 mg, 5.224 mmol) and ACN (100 mL) were added to a 250 mL single-necked flask, and a solution of Boc$_2$O (14.82 g, 67.92 mmol) in ACN (30 mL) was then added dropwise at room temperature. After the dropwise addition was completed, the reaction system was stirred at room temperature for 3 h. After the completion of the reaction as detected by LC-MS, the reaction solution was concentrated under reduced pressure, and the residue was purified by column chromatography (EA/PE=1/20 to 1/10) to give the product in the form of a colorless liquid (13.5 g, 95% yield), ESI-MS m/z: 272.0 [M+H]$^+$.

1-(tert-butyl)4-methyl 4-((6-bromo-3-fluoropyridin-2-yl)methyl)-2-ethylpiperidine-1,4-dicarboxylic acid (30-B)

30-A (10.5 g, 38.9 mmol) and anhydrous THF (200 mL) were added to a 500 mL three-necked flask, and the reaction system was cooled to −60° C. under Ar atmosphere. LDA (29.2 mL, 2 M in THF, 58.4 mmol) was added dropwise slowly, and the temperature was kept below −50° C. during the dropwise addition. After the dropwise addition was completed, the mixed solution was stirred at −60±10° C. for 1.5 h. A solution of 6-bromo-2-(bromomethyl)-3-fluoropyridine (12.55 g, 46.68 mmol) in THF (50 mL) was then added dropwise at −60±10° C. After the dropwise addition was completed, the resulting reaction system was stirred at −60±10° C. for 1 h, and then slowly warmed to room temperature and reacted for 1 h. After the completion of the reaction as detected by TLC (EA/PE=1/5) and LC-MS, ammonium chloride solution (100 mL) was added to quench the reaction, and EA (100 mL×2) was added for extraction. The organic phases were combined, washed with saturated sodium chloride solution (100 mL×2) and concentrated, and the residue was purified by column chromatography (EA/PE=1/20 to 1/10) to give the product in the form of a yellow liquid (12.87 g, 72% yield), ESI-MS m/z: 459.0/461.0 [M+H]$^+$.

1-(tert-butyl)4-methyl-2-ethyl-4-((3-fluoro-6-(thiazol-2-ylamino)pyridin-2-yl)methyl)-piperidine-1,4-dicarboxylate (30-C)

30-B (6.2 g, 13.5 mmol), 2-aminothiazole (1.35 g, 13.5 mmol), anhydrous potassium phosphate (7.2 g, 34.0 mmol), Xantphos (780 mg, 1.35 mmol) and Dioxane (100 mL) were added to a 250 mL single-necked flask. After purge with Ar, Pd$_2$(dba)$_3$ (617 mg, 0.675 mmol) was added, and the reaction system was warmed to reflux under Ar atmosphere and reacted for 5 h. After the completion of the reaction as detected by LC-MS, the reaction system was concentrated under reduced pressure, and the residue was purified by column chromatography (DCM/MeOH=40/0 to 40/1) to give a brown solid (5.23 g, 81% yield), ESI-MS m/z: 479.2 [M+H]$^+$.

Methyl 2-ethyl-4-((3-fluoro-6-(thiazol-2-ylamino) pyridin-2-yl)methyl)piperidine-4-carb-oxylate dihydrochloride (30-D)

30-C (5 g, 10.46 mmol), DCM (20 mL) and HCl/Dioxane (26 mL, 4 M, 104 mmol) were added to a 100 mL single-necked flask, and the reaction system was stirred at room temperature for 20 h. After the completion of the reaction as detected by LC-MS, the reaction solution was concentrated, and the residue was added to EA (30 mL). The mixture was stirred at room temperature for 30 min, filtered and dried over anhydrous Na$_2$SO$_4$ to give the product in the form of a yellow solid (4.8 g, 100% yield), ESI-MS m/z: 379.2 [M+H]$^+$.

Methyl 1-(2,3-difluorobenzyl)-2-ethyl-4-((3-fluoro-6-(thiazol-2-ylamino)pyridin-2-yl)-methyl)piperidine-4-carboxylate (30-E)

30-D (413 mg, 0.92 mmol), 1-(bromomethyl)-2,3-difluorobenzene (226 mg, 1.1 mmol), $K_2CO_3$ (632 mg, 4.58 mmol), KI (20 mg) and ACN (10 mL) were added to a 100 mL single-necked flask, and the reaction system was reacted at room temperature for about 2 h. After the completion of the reaction as detected by LC-MS, water (100 mL) was added, and solids were precipitated out. The mixture was subjected to suction filtration, and the filter cake was washed with water (20 mL×2). The mixture was slurried with PE (50 mL) and then subjected to suction filtration. The filter cake was washed with PE (20 mL×2) and air dried to give the product (295 mg, 64% yield), ESI-MS m/z: 505.1 [M+H]$^+$.

1-(2,3-difluorobenzyl)-2-ethyl-4-((3-fluoro-6-(thiazol-2-ylamino)pyridine-2-yl)methyl) piperidine-4-carboxylic acid (30)

30-E (295 mg, 0.585 mmol), water (5 mL) and concentrated HCl (5 mL) were added to a 100 mL single-necked flask, and the reaction system was refluxed at 105° C. for 20 h. After the completion of the reaction as detected by LC/MS, the reaction solution was concentrated to dryness under reduced pressure, and the residue was added to ACN (30 mL). The mixture was slurried at room temperature and subjected to suction filtration, and the filter cake was washed with ACN (5 mL×2) and air dried to give the product in the form of a light yellow powder (118 mg, 41% yield).

$^1$H NMR (400 MHz, DMSO-d$_6$) δ11.31 (s, 1H), 9.15 (s, 1H), 7.85-7.72 (m, 2H), 7.59-7.45 (m, 1H), 7.33-7.19 (m, 2H), 7.05-6.92 (m, 2H), 4.75 (d, J=13.4 Hz, 1H), 4.26-4.10 (m, 1H), 3.24-3.06 (m, 2H), 2.96-2.73 (m, 2H), 2.41 (d, J=13.7 Hz, 1H), 2.21-2.02 (m, 2H), 1.92-1.56 (m, 4H), 0.91 (dt, J=10.8 7.3 Hz, 3H); ESI-MS m/z: 491.1 [M+H]$^+$.

Examples 31-34. Synthesis of Compounds 31-34

The target compounds 31-34 were obtained according to a similar synthesis method as in Example 30 using different starting materials.

TABLE 2

| Compound | Compound structure | Name | [M + H]$^+$ |
|---|---|---|---|
| 31 | 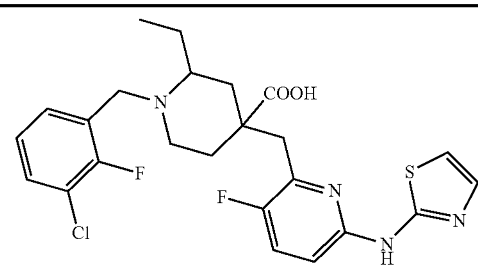 | 2-ethyl-1-(2-fluoro-3-(trifluoromethyl)benzyl)-4-((3-fluoro-6-(thiazol-2-ylamino)yridine-2-yl)methyl)piperidine-4-carboxylic acid | 541.2 |
| 32 | 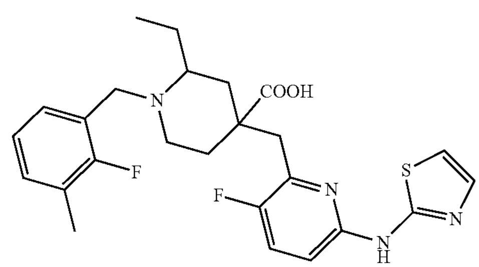 [SMILES: CCC1CC(Cc2nc(Nc3nccs3)ccc2F)(C(=O)O)CCN1Cc1cccc(C)c1F] | 2-ethyl-1-(2-fluoro-3-methylbenzyl)-4-((3-fluoro-6-(thiazol-2-ylamino)pyridine-2-yl)methyl)piperidine-4-carboxylic acid | 487.2 |
| 33 | 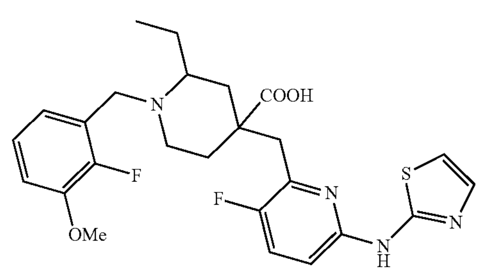 [SMILES: CCC1CC(Cc2nc(Nc3nccs3)ccc2F)(C(=O)O)CCN1Cc1cccc(OC)c1F] | 2-ethyl-1-(2-fluoro-3-methoxybenzyl)-4-((3-fluoro-6-(thiazol-2-ylamino)pyridine-2-yl)methyl)piperidine-4-carboxylic acid | 503.2 |
| 34 | 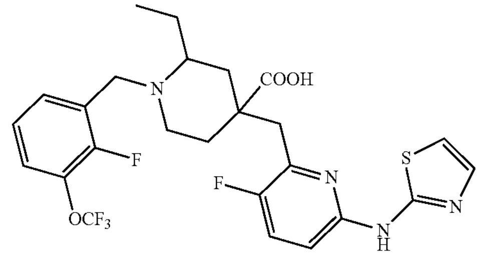 [SMILES: CCC1CC(Cc2nc(Nc3nccs3)ccc2F)(C(=O)O)CCN1Cc1cccc(OC(F)(F)F)c1F] | 2-ethyl-1-(2-fluoro-3-(trifluoromethoxy)benzyl)-4-((3-fluoro-6-(thiazol-2-ylamino)pyridine-2-yl)methyl)piperidine-4-carboxylic acid | 557.2 |

Example 35. Synthesis of 1-(3-chloro-2-fluorobenzoyl)-4-((3-fluoro-6-(thiazol-2-ylamino) pyridin-2-yl)methyl)-2-(trifluoromethyl)piperidine-4-carboxylic acid (compound 35)

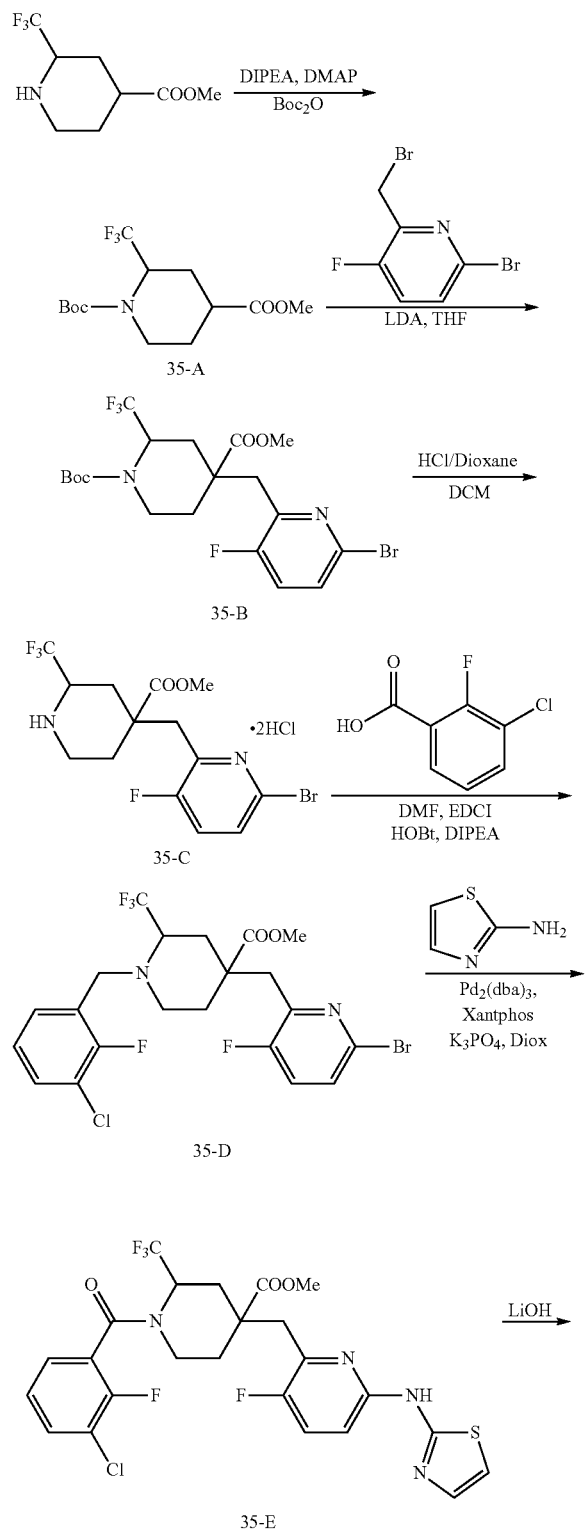

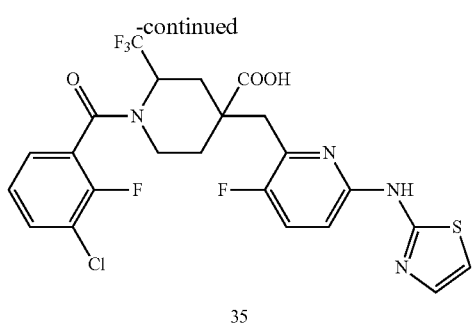

1-(tert-butyl)4-methyl 2-(trifluoromethyl)piperidine-1,4-dicarboxylate (35-A)

Methyl 2-(trifluoromethyl)piperidine-4-carboxylate (2.11 g, 10 mmol), DIPEA (3.87 g, 30 mmol), DMAP (244 mg, 24 mmol) and CAN (50 mL) were added to a 250 mL single-necked flask, and a solution of Boc$_2$O (3.27 g, 15 mmol) in ACN (30 mL) was then added dropwise at room temperature. After the dropwise addition was completed, the reaction system was warmed to reflux and stirred for 3 h. After the completion of the reaction as detected by LC-MS, the reaction solution was concentrated under reduced pressure, and the residue was purified by column chromatography (EA/PE=1/20 to 1/10) to give the product in the form of a colorless liquid (2.3 g, 74% yield), ESI-MS m/z: 312.0 [M+H]$^+$.

1-(tert-butyl)4-methyl 4-((6-bromo-3-fluoropyridin-2-yl)methyl)-2-(trifluoromethyl) piperidine-1,4-dicarboxylic acid (35-B)

35-A (2.2 g, 7.07 mmol) and anhydrous THF (50 mL) were added to a 250 mL three-necked flask, and the reaction system was cooled to −60° C. under Ar atmosphere. LDA (5.3 mL, 2 M in THF, 10.6 mmol) was added dropwise slowly, and the temperature was kept below −50° C. during the dropwise addition. After the dropwise addition was completed, the mixed solution was stirred at −60±10° C. for 1.5 h. A solution of 6-bromo-2-(bromomethyl)-3-fluoropyridine (2.09 g, 7.777 mmol) in THF (50 mL) was then added dropwise at −60±10° C. After the dropwise addition was completed, the resulting reaction system was stirred at −60±10° C. for 1 h, and then slowly warmed to room temperature and reacted for 1 h. After the completion of the reaction as detected by TLC (EA/PE=1/5) and LC-MS, ammonium chloride solution (100 mL) was added to quench the reaction, and EA (100 mL×2) was added for extraction. The organic phases were combined, washed with saturated sodium chloride solution (100 mL×2) and concentrated, and the residue was purified by column chromatography (EA/PE=1/20 to 1/10) to give the product in the form of a yellow liquid (2.58 g, 73% yield), ESI-MS m/z: 499.0/501.0 [M+H]$^+$.

Methyl 4-((6-bromo-3-fluoropyridin-2-yl)methyl)-2-(trifluoromethyl)piperidine-4-carb-oxylate dihydrochloride (35-C)

35-B (2.5 g, 5.01 mmol), DCM (25 mL) and HCl/Dioxane (12.5 mL, 4 M, 50 mmol) were added to a 100 mL single-necked flask, and the reaction system was stirred at room temperature for 20 h. After the completion of the reaction as detected by LC-MS, the reaction solution was concentrated, and the residue was added to EA (10 mL). The mixture was stirred at room temperature for 30 min, filtered and dried over anhydrous $Na_2SO_4$ to give the product in the form of a yellow solid (1.68 g, 71% yield), ESI-MS m/z: 399.0/401.0 [M+H]+.

Methyl 4-((6-bromo-3-fluoropyridin-2-yl)methyl)-1-(3-chloro-2-fluorobenzoyl)-2-(trifluoromethyl)piperidine-4-carboxylate (35-D)

35-C (1.68 g, 3.56 mmol), DMF (30 mL), DIPEA (2.3 g, 17.8 mmol), EDCI (1.023 g, 5.34 mmol), HOBt (721 mmol, 5.34 mmol) and 3-chloro-2-fluorobenzoic acid (746 mg, 4.27 mmol) were added to a 100 mL single-necked flask, and the reaction system was stirred at 50° C. for 20 h under Ar atmosphere. After the completion of the reaction as detected by LC-MS, EA (50 mL) and $H_2O$ (50 mL) were added to the reaction system. The resulting reaction system was stirred, and liquid separation was performed. The organic phase was concentrated to dryness, and the residue was purified by column chromatography (EA/PE=1/20 to 1/10) to give the product (1.4 g, 71% yield), ESI-MS m/z: 555.0/557.0 [M+H]+.

Methyl 1-(3-chloro-2-fluorobenzoyl)-4-(3-fluoro-6-(thiazol-2-ylamino)pyridin-2-yl)-methyl)-2-(trifluoromethyl)piperidine-4-carboxylate (35-E)

35-D (200 mg, 0.36 mmol), 2-aminothiazole (36 mg, 0.36 mmol), anhydrous $K_2CO_3$ (124 g, 0.9 mmol), Xantphos (42 mg, 0.072 mmol) and Dioxane (10 mL) were added to a 250 mL single-necked flask. After purge with Ar, $Pd_2(dba)_3$ (33 mg, 0.036 mmol) was added, and the reaction system was warmed to reflux under Ar atmosphere and reacted for 5 h. After the completion of the reaction as detected by LC-MS, the reaction system was concentrated under reduced pressure, and the residue was purified by column chromatography (DCM/MeOH=40/0 to 40/1) to give a brown solid (126 mg, 61% yield), ESI-MS m/z: 575.1 [M+H]+.

1-(3-chloro-2-fluorobenzoyl)-4-(3-fluoro-6-(thiazol-2-ylamino)pyridin-2-yl)methyl)-2-(trifluoromethyl)piperidine-4-carboxylic acid (35)

35-E (120 mg, 0.208 mmol), THF (5 mL), water (2 mL) and $LiOH \cdot H_2O$ (88 mg, 2.1 mmol) were added to a 100 mL single-necked flask, and then the reaction system was warmed to 50° C. under Ar atmosphere and reacted for about 5 h. After the completion of the reaction as detected by LC/MS, the reaction solution was adjusted to pH=4-5 and concentrated under reduced pressure, and the residue was purified by Flash column chromatography to give the product in the form of a light yellow powder (28 mg, 24% yield).

$^1H$ NMR (400 MHz, $CD_3OD$) δ7.78 (t, J=9.0 Hz, 1H), 7.61-7.52 (m, 2H), 7.41 (dt, J=12.0, 7.9 Hz, 1H), 7.26 (d, J=7.5 Hz, 1H), 7.20 (d, J=4.3 Hz, 1H), 7.12 (dd, J=8.9, 3.0 Hz, 1H), 4.52-4.47 (m, 1H), 4.26-4.12 (m, 1H), 3.50-3.38 (m, 2H), 3.25-3.19 (m, 2H), 2.39-2.31 (m, 1H), 2.25-2.19 (m, 1H), 2.11-2.04 (m, 1H), 1.95-1.84 (m, 1H); ESI-MS m/z: 561.1 [M+H]+.

Examples 36 and 37. Synthesis of Compounds 36 and 37

The target compounds 36 and 37 were obtained according to a similar synthesis method as in Example 35 using different starting materials.

TABLE 3

| Compound | Compound structure | Name | [M + H]+ |
|---|---|---|---|
| 36 | 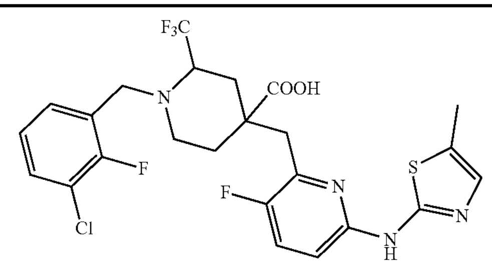 | 1-(3-chloro-2-fluorobenzoyl)-4-((3-fluoro-6-((5-methylthiazol-2-yl)amino)pyridin-2-yl)methyl)-2-(trifluoromethyl)piperidine-4-carboxylic acid | 575.1 |
| 37 | 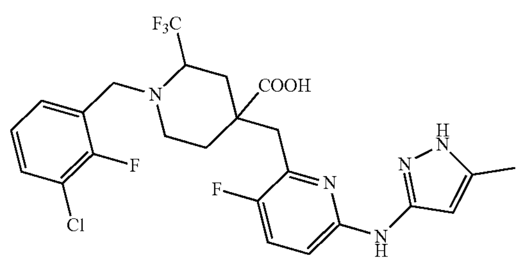 [SMILES: Cc1cc(Nc2ccc(F)c(CC3(C(=O)O)CCN(Cc4cccc(Cl)c4F)C(C(F)(F)F)C3)n2)n[nH]1] | 1-(3-chloro-2-fluorobenzoyl)-4-(3-fluoro-6-((5-methyl-1H-pyrazol-3-yl)amino)pyridin-2-yl)methyl)-2-(trifluoromethyl)piperidine-4-carboxylic acid | 558.1 |

Example 38. Assay for Inhibitory Activity Against Aurora Kinase

In vitro assay for inhibitory activity of the compounds disclosed herein against aurora kinase activity was performed using the Caliper Mobility Shift method. The compounds were each subjected to gradient dilution from 10 μM to obtain a total of 10 concentrations. After the enzyme and kinase reaction solution (20 mM HEPES, pH 7.5, 0.01% Triton X-100) were mixed, the gradiently diluted compound was added. The mixture was incubate at room temperature for 10 min to allow the compound and enzyme to bind well. Then, FAM-labeled polypeptide was added as a substrate to carry out a kinase reaction at 25° C., and after a certain time, a stop solution was added. The conversion rates were read using a Caliper and converted into inhibition rates, and $IC_{50}$ values were calculated, wherein a blank solvent without drug was used as a negative control, and LY-3295668 was used as a positive control. The results of the above compounds are shown in Table 4.

Example 39. Assay for Anti-Proliferation Activity Against 1169 Cells

Tumor cells (human small cell lung cancer H69 cells) in logarithmic growth phase were seeded into a 384-well culture plate at $4 \times 10^3$ cells per well, 50 μL of medium was added to each well, and the mixtures were cultured overnight in a 37° C./5% $CO_2$ incubator. After the cells adhered to the wall, the test compounds and the positive control drug at proper concentrations were each added, and five samples with different concentrations were prepared. A blank group was taken as a negative control group, and the resulting mixtures were cultured in an incubator for 72 h. 50 μL of CTL plus was then added to each well, and the number of cells was evaluated by measuring ATP content in the cells. The $IC_{50}$ values were calculated by fitting with GRAPH-PAD, and the results are shown in Table 4.

TABLE 4

Activity of part of the compounds disclosed herein against aurora kinase and their anti-proliferation activity against H69 cells

| Compound | Aurora, $IC_{50}$ (nM) | | H69, $IC_{50}$ (μM) |
| --- | --- | --- | --- |
| | A | B | |
| 1 | 0.53 | 148 | 0.011 |
| 5 | 0.82 | 140 | 0.033 |
| 6 | 0.57 | 78 | 0.049 |
| 7 | 0.74 | 286 | 0.052 |
| 11 | 2.4 | 128 | 0.019 |
| 13 | 0.64 | 113 | 0.59 |
| 15 | 0.62 | 1488 | 0.77 |
| 19 | 3.1 | >3000 | 0.219 |
| 23 | 0.57 | 2468 | 0.058 |
| 25 | 0.78 | >3000 | 0.098 |
| 29 | 1.3 | 90 | 0.024 |
| LY-3295668 | 1.7 | 2259 | 0.063 |

The above data indicate that the compounds disclosed herein have higher activity against aurora kinase and anti-cell proliferation activity than those of the control drug LY-3295668, and the compounds of formula (1) have extremely high activity against Aurora-A kinase and greatly improve activity against Aurora-B kinase and anti-proliferation activity against H1975 cells when the $R^3$ group is changed from Me to a relatively large group or is substituted with a strong electron-withdrawing group, such as $CF_3$, and/or when W is

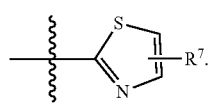

Example 40. Evaluation of Anti-Tumor Activity in Mice

Human lung cancer H69 cells were cultured conventionally in 1640 medium containing 10% fetal bovine serum in a 37° C./5% $CO_2$ incubator, and then the cells were passaged and collected when they reached the desired amount. $1 \times 10^7$ H69 cells were injected into the right dorsal side of each nude mouse, and the animals were randomly grouped for administration after tumors grew to 150 $mm^3$. The groups were: 1) solvent control group, 8 mice; 2) LY-3295668 group, compound 1 group, compound 5 group and compound 6 group, 8 mice for each. Mice in the solvent control group were subjected to intragastric administration of 0.5% CMC-Na twice daily, and mice in the LY-3295668 group, the compound 1 group, the compound 5 group and the compound 6 group were subjected to intragastric administration of a suspension of compound in 0.5% CMC-Na twice daily. On Tuesday and Thursday each week, tumor volumes and body weight of mice were measured, and the nude mice were sacrificed on day 21 of administration. The test results are shown in Table 5 below.

TABLE 5

Experimental therapeutic effect of compounds on graft tumors of human non-small cell lung adenocarcinoma NCI-H69 in nude mice

| Compound | Dosage (mg/kg) | Administration regimen | Anti-tumor effect |
| --- | --- | --- | --- |
| 1 | 20 | bid*21 | 29% shrinking |
| 5 | 20 | bid*21 | 9% shrinking |
| 6 | 20 | bid*21 | 30% shrinking |
| LY-3295668 | 20 | bid*21 | 15% shrinking |

As can be seen from Table 5 above, compound 1 and compound 6 show significantly increased in vivo anti-tumor activity compared with the positive control LY-3295668, which indicates that the compounds of formula (1) have greatly increased in vivo anti-tumor activity when the $R^3$ group is changed from Me to a group with proper size, such as $CF_3$ or —$CH_2OMe$, and/or when W is

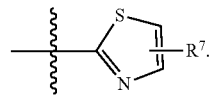

The invention claimed is:

1. A compound of formula (1), an optical isomer, a crystalline form or a pharmaceutically acceptable salt or ester thereof:

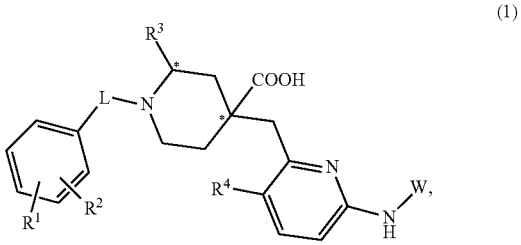

wherein in the formula (1):
"*" indicates a chiral center;
L is $CH_2$ or CO;
$R^1$ and $R^2$ are independently H, halogen, CN, C1-C3 alkyl, C3-C6 cycloalkyl, C1-C3 alkoxy, C1-C3 haloalkyl and C1-C3 haloalkoxy;

R³ is C2-C3 alkyl, C3-C6 cycloalkyl, C1-C3 haloalkyl, —(C1-C3)alkyl-OH, —(C1-C3)alkyl-(C1-C3)alkoxy, —(C1-C3)alkyl-CN or —(C1-C3)alkyl-NR⁵R⁶, wherein R⁵ and R⁶ are independently H or C1-C3 alkyl, or R⁵ and R⁶ form a 4-7 membered heterocycloalkyl together with an N atom;

R⁴ is H or F;

W is

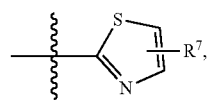

wherein R⁷ is H, C1-C3 alkyl or C3-C6 cycloalkyl.

2. The compound according to claim 1, wherein in the formula (1),

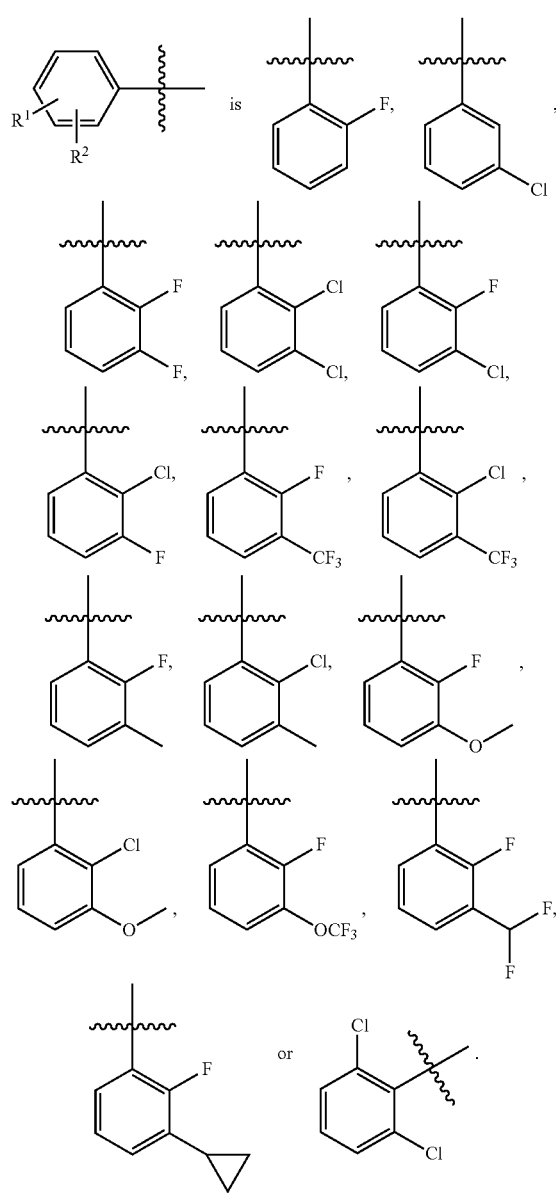

3. The compound according to claim 1, wherein in the formula (1), R³ is Et, ⁿ-Pr, ⁱ-Pr,

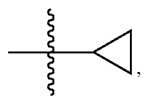

CH₂F, CHF₂, CF₃, CH₂OH, CH₂OMe, CH₂OEt, CH₂CN,

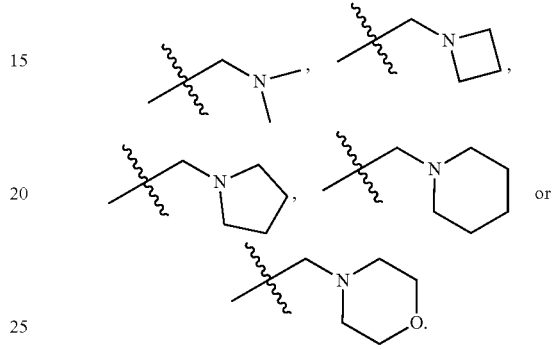

4. The compound according to claim 1, wherein in the formula (1), W is

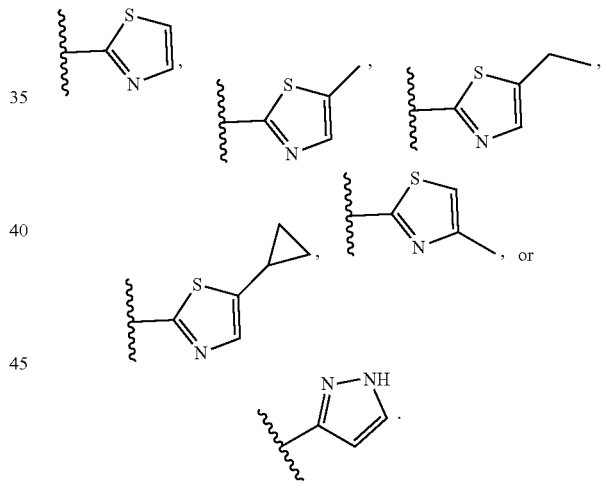

5. The compound according to claim 1, or a pharmaceutically acceptable salt or ester thereof, wherein the compound is:

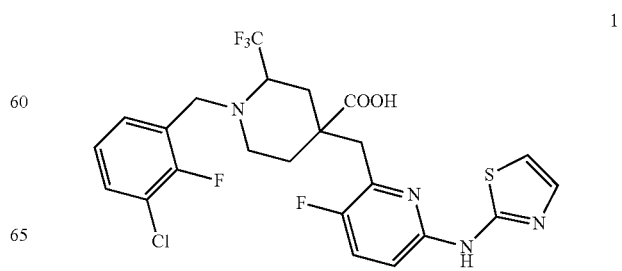

47
-continued
2
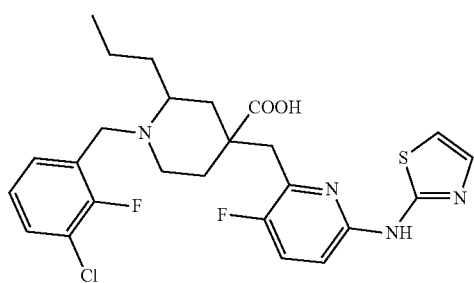
3
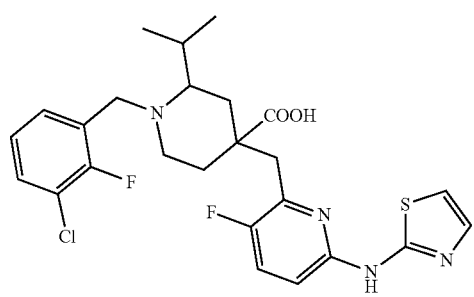
4
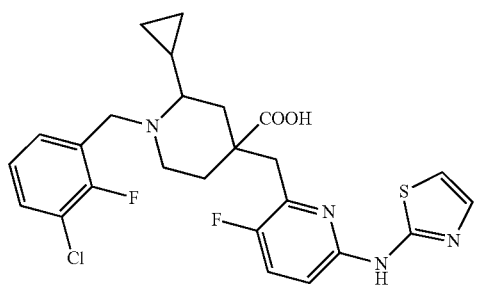
5
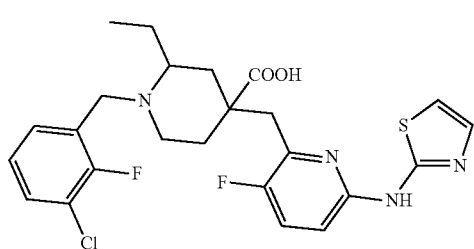
6
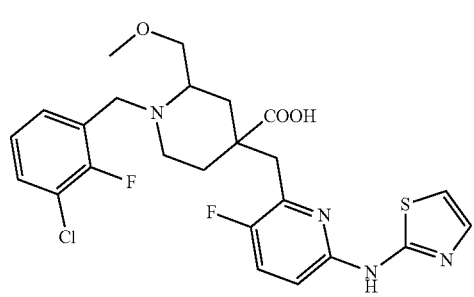
48
-continued
7
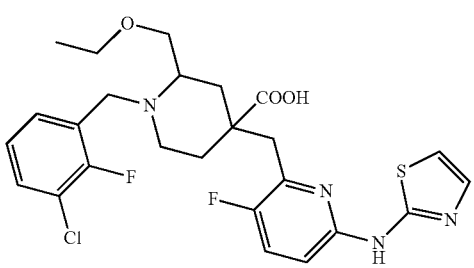
8
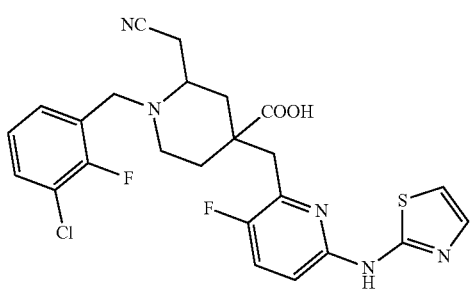
9
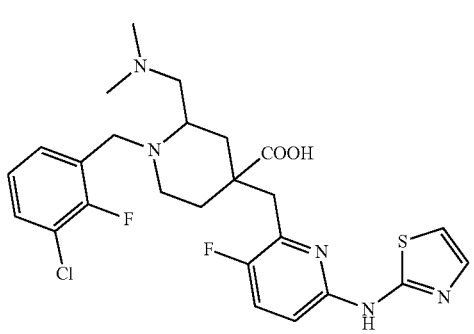
10
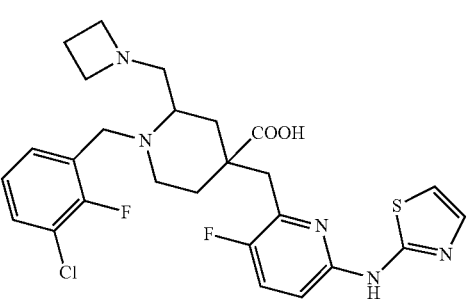
11
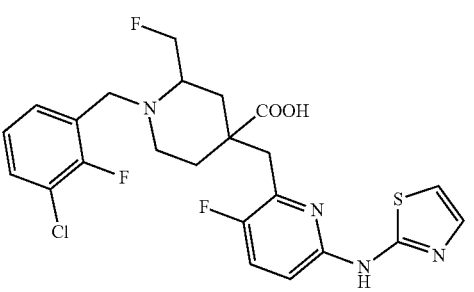

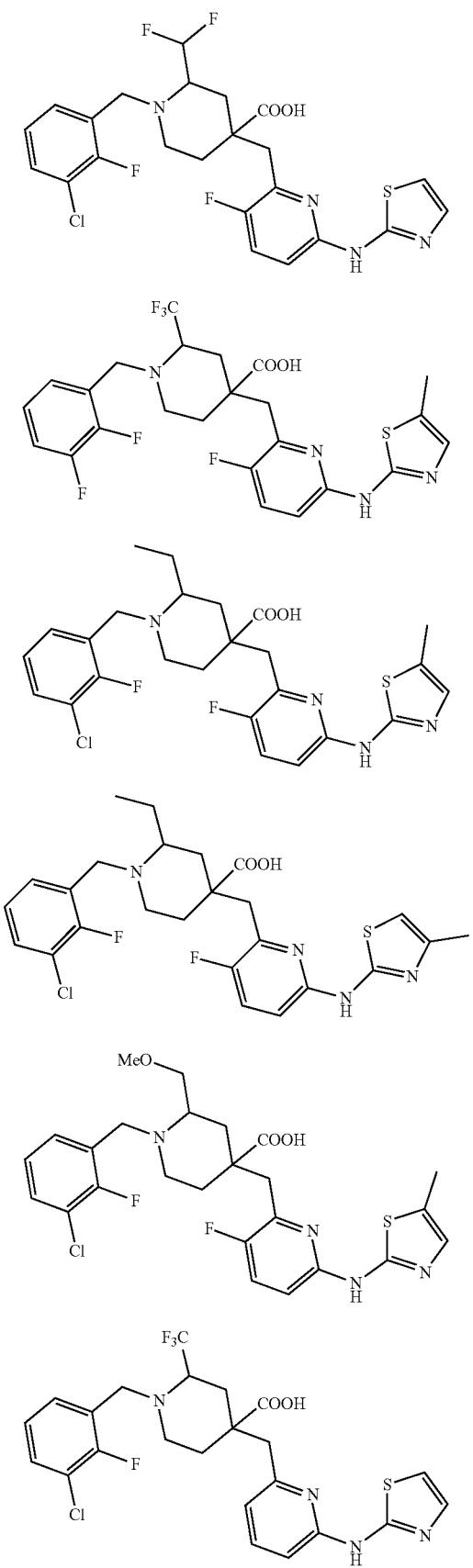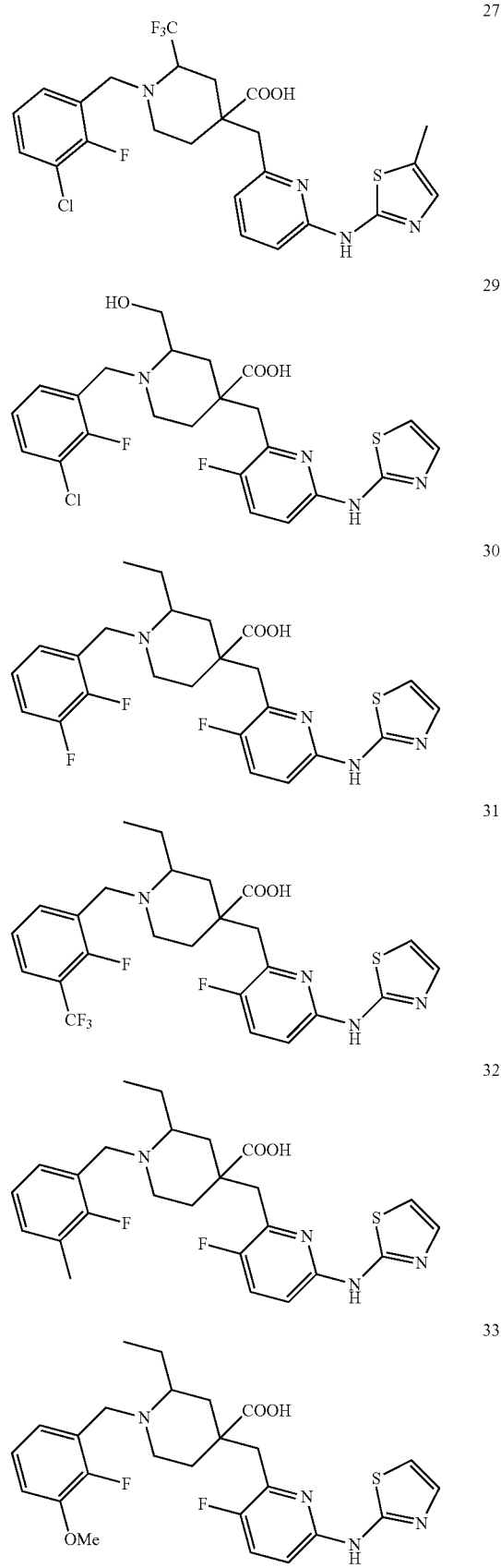

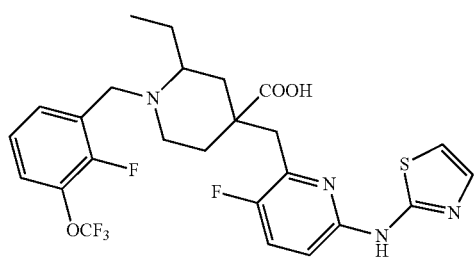

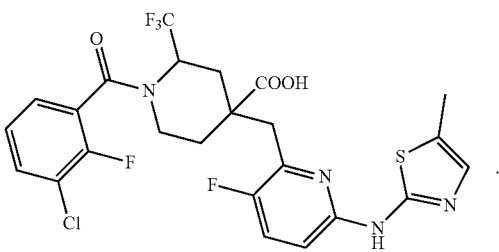

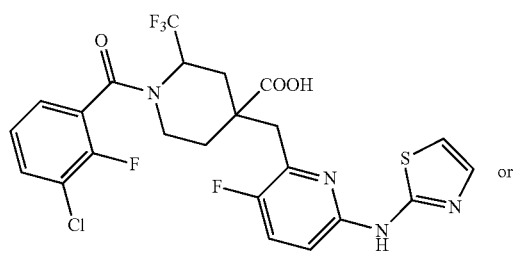 or

6. An aurora kinase inhibitor comprising the compound according to claim 1, an optical isomer, a crystalline form or a pharmaceutically acceptable salt or ester thereof as an active ingredient.

7. A pharmaceutical composition comprising the compound according to claim 1, an optical isomer, a crystalline form or a pharmaceutically acceptable salt or ester thereof as an active ingredient and comprising a pharmaceutically acceptable carrier or diluent.

* * * * *